US010561742B2

(12) United States Patent
Chen et al.

(10) Patent No.: US 10,561,742 B2
(45) Date of Patent: *Feb. 18, 2020

(54) METHODS AND COMPOSITIONS FOR TREATMENT OF DISEASE OR INJURY OF THE NERVOUS SYSTEM

(71) Applicant: The Penn State Research Foundation, University Park, PA (US)

(72) Inventors: Gong Chen, State College, PA (US); Ziyuan Guo, State College, PA (US); Zheng Wu, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 418 days.

This patent is subject to a terminal disclaimer.

(21) Appl. No.: 13/946,419

(22) Filed: Jul. 19, 2013

(65) Prior Publication Data

US 2014/0024599 A1     Jan. 23, 2014

Related U.S. Application Data

(60) Provisional application No. 61/762,506, filed on Feb. 8, 2013, provisional application No. 61/673,471, filed on Jul. 19, 2012.

(51) Int. Cl.
*C12N 15/86* (2006.01)
*A61K 48/00* (2006.01)
*A61K 38/17* (2006.01)

(52) U.S. Cl.
CPC ........ *A61K 48/005* (2013.01); *A61K 38/1709* (2013.01); *C12N 15/86* (2013.01)

(58) Field of Classification Search
None
See application file for complete search history.

(56) References Cited

U.S. PATENT DOCUMENTS

| 5,695,995 | A | 12/1997 | Weintraub et al. |
| 6,444,463 | B1 | 9/2002 | Tapscott |
| 7,041,507 | B1 | 5/2006 | Levesque et al. |
| 9,717,804 | B2 | 8/2017 | Chen et al. |
| 2013/0022583 | A1* | 1/2013 | Wernig et al. ............... 424/93.7 |

FOREIGN PATENT DOCUMENTS

| WO | WO-2011050476 | 5/2011 |
| WO | WO-2011097181 | 8/2011 |
| WO | WO2012010675 | * 1/2012 |

OTHER PUBLICATIONS

Escartin et al (Mol Neurobiol 38: 231-241, 2008).*
Kitagawa (Rinsho Shinkeigaku 44: 756-759, 2004—abstract only).*
Richardson et al Neurosurg Clin N Am 20: 219-224, 2009.*
Roybon, L. et al., Neurogenin2 Directs Granule Neuroblast Production and Amplification While NeurodD1 Specifies Neuronal Fate During Hippocampal Neurogenesis, Plos One, 4(3): 1-19, Mar. 10, 2009.
Cho, J. et al., the Role of BETA2/NeuroD1 in the Development of the Nervous System, *Molecular Neurobiology*, 30(1): 35-47, 2004.
Gao, Z. et al., Neurodl is essential for the survival and maturation of adult-born neurons, 12(9): 1090-1092, Sep. 2009.
Torper, O. et al., Generation of induced neurons via direct conversion in vivo, PNAS Early Edition, Mar. 25, 2013.
Zhao, J. et al., Neuronal Transcription Factors Induce Conversion of Human Glioma Cells to Neurons and Inhibit Tumorigenesis, *PLoS One*, 7(7): 1-11, Jul. 31, 2012.
Gallo, V. et al., Ghial Development: The Crossroads of Regeneration and Repair in the CNS, *Neuron*, 83: 285-308, Jul. 16, 2014.
Guo, Z. et al., In Vivo Direct Reprogramming of Reactive Glial Cells into Functional Neurons after Brain Injury and in an Alzheimer's Disease Model, *Cell Stem Cell*, 14: 188-202, Feb. 6, 2014.
Lu, J. et al., Turning Reactive Glia into Functional Neurons in the Brain, *Cell Stem Cell*, 14: 133-34, Feb. 6, 2014.
Yang, N. et al., Induced Neuronal Cells: How to Make and Define a Neuron, *Cell Stem Cell*, 9: 517-525, Dec. 2, 2011.
Lee, J. et al., Conversion of Xenopus Ectoderm into Neurons by NeuroD, a Basic Helix-Loop-Helix Protein, *Science*, 268: 836-44, May 12, 1995.
Fang Hongbo, the Molecular Mechanism of the NeuroD1 Gene Regulation Induced by All-trans Retinoic Acid in Neural Cells Differentiation, China Doctor Dissertation Full-text Database (Electronic Journal) Basic Science Volume, No. 11, pp. A006-4, published on Nov. 15, 2011.
Chinese Application No. 201380048924.2, Office Action dated Jun. 17, 2016, Chinese Language.
Chinese Application No. 201380048924.2, Office Action dated Jun. 17, 2016, English Language.
Chinese Application No. 201380048924.2, Office Action dated Mar. 21, 2017, Chinese Language.
Chinese Application No. 201380048924.2, Office Action dated Mar. 21, 2017, English Language.
Yokoyama, M. et al., Molecular cloning of a human neuroD from a neuroblastoma cell line specifically expressed in the fetal brain and adult cerebellum, *Molecular Brain Research*, 42: 135-139, 1996.
English abstract of Fang Hongbo, The Molecular Mechanism of the NeuroD1 Gene Regulation Induced by All-trans Retinoic Acid in Neural Cells Differentiation, China Doctor Dissertation Full-text Database (Electronic Journal) Basic Science Volume, No. 11, pp. A006-4, published on Nov. 15, 2011.

(Continued)

*Primary Examiner* — Daniel E Kolker
*Assistant Examiner* — Aditi Dutt
(74) *Attorney, Agent, or Firm* — Fish & Richardson P.C.

(57) ABSTRACT

Methods for producing new neurons in the brain in vivo are provided according to aspects of the present invention which include introducing NeuroD1 into a glial cell, particularly into a reactive astrocyte or NG2 cell, thereby "converting" the reactive glial cell to a neuron. Methods of producing a neuronal phenotype in a glial cell are provided according to aspects of the present invention which include expressing exogenous NeuroD1 in the glial cell, wherein expressing exogenous NeuroD1 includes delivering an expression vector, such as a viral expression vector, including a nucleic acid encoding the exogenous NeuroD1 to the glial cell.

5 Claims, 17 Drawing Sheets

Specification includes a Sequence Listing.

(56) References Cited

OTHER PUBLICATIONS

Altschul et al., "Basic local alignment search tool," J. Mol. Biol., 215(3):403-10, Oct. 1990.

Altschul et al., "Gapped BLAST and PSI-BLAST: A new generation of protein database search programs," Nucleic. Acids. Res., 25(17):3389-402, Sep. 1997.

Chinese Application No. 201380048924.2, Office Action dated Apr. 13, 2018, English Language.

Chinese Application No. 201380048924.2, Office Action dated Sep. 26, 2017, English Language.

Deng et al., "Sequential postsynaptic maturation governs the temporal order of GABAergic and glutamatergic synaptogenesis in rat embryonic cultures," J. Neurosci., 27(40):10860-10869, Oct. 2007.

Heinrich et al., "Directing astroglia from the cerebral cortex into subtype specific functional neurons," PLoS Biol, 8(5):e1000373, May 2010.

Karlin and Altschul, "Applications and statistics for multiple high-scoring segments in molecular sequences," PNAS, 90(12):5873-5877, Jun. 1993.

Karlin and Altschul, "Methods for assessing the statistical significance of molecular sequence features by using general scoring schemes," PNAS, 87(6):2264-2268, Mar. 1990.

Kuwabara et al., "Wnt-mediated activation of NeuroD1 and retroelements during adult neurogenesis," Nat. Neurosci., 12(9):1097-1105, Sep. 2009.

Myers and Miller, "Optimal alignments in linear space," Comput. Appl. Biosci., 4(1):11-17, Mar. 1988.

Oakley et al., "Intraneuronal beta-amyloid aggregates, neurodegeneration, and neuron loss in transgenic mice with five familial Alzheimer's disease mutations: potential factors in amyloid plaque formation," J. Neurosci., 26(40):10129-40, Oct. 2006.

Richardson et al., "NG2-glia as multipotent neural stem cells: fact or fantasy?" Neuron, 70(4):661-673, May 2011.

www.sciencemag.org [online], "Reprogrammed cells could tackle brain damage," Nov. 14, 2018, [retrieved on Jun. 25, 2019], retrieved from: URL<https://www.sciencemag.org/news/2018/11/reprogrammed-cells-could-tackle-brain-damage>, 11 pages.

Zernicka-Goetz et al., "Following cell fate in the living mouse embryo," Development, 124(6):1133-1137, Mar. 1997.

Zhao et al., "Distinct morphological stages of dentate granule neuron maturation in the adult mouse hippocampus," J. Neurosci., 26(1):3-11, Jan. 2006.

* cited by examiner

SEQUENCE LISTING

<160> NUMBER OF SEQ ID NOS: 4

<210> SEQ ID NO 1
<211> LENGTH: 1071
<212> TYPE: DNA
<213> ORGANISM: Homo sapiens

<400> SEQUENCE: 1

```
atgaccaaat cgtacagcga gagtgggctg atgggcgagc ctcagcccca aggtcctcca      60
agctggacag acgagtgtct cagttctcag gacgaggagc acgaggcaga caagaaggag     120
gacgacctcg aagccatgaa cgcagaggag gactcactga ggaacggggg agaggaggag     180
gacgaagatg aggacctgga agaggaggaa gaagaggaag aggaggatga cgatcaaaag     240
cccaagagac gcggcccaa aaagaagaag atgactaagg ctcgcctgga gcgttttaaa     300
ttgagacgca tgaaggctaa cgcccgggag cggaaccgca tgcacggact gaacgcggcg     360
ctagacaacc tgcgcaaggt ggtgccttgc tattctaaga cgcagaagct gtccaaaatc     420
gagactctgc gcttggccaa gaactacatc tgggctctgt cggagatcct gcgctcaggc     480
aaaagcccag acctggtctc cttcgttcag acgctttgca agggcttatc ccaacccacc     540
accaacctgg ttgcgggctg cctgcaactc aatcctcgga ctttctctgcc tgagcagaac     600 caggacatgc cccccacct gccgacggcc agcgcttcct tccctgtaca ccctactcc     660 taccagtcgc ctgggctgcc cagtccgcct acggtacca tggacagctc ccatgtcttc     720
cacgttaagc ctccgccgca cgcctacagc gcagcgctgg agcccttctt tgaaagccct     780
ctgactgatt gcaccagccc ttcctttgat ggaccctca gcccgccgct cagcatcaat     840
ggcaacttct ctttcaaaca cgaaccgtcc gccgagtttg agaaaaatta tgcctttacc     900
atgcactatc ctgcagcgac actggcaggg gcccaaagcc acggatcaat cttctcaggc     960
```

```
accgctgccc ctcgctgcga gatccccata gacaatatta tgtccttcga tagccattca    1020
catcatgagc gagtcatgag tgcccagctc aatgccatat ttcatgatta g             1071
```

<210> SEQ ID NO 2
<211> LENGTH: 356
<212> TYPE: PRT
<213> ORGANISM: Homo sapiens

<400> SEQUENCE: 2

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Asp Asp Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350
```

Ile Phe His Asp
       355

<210> SEQ ID NO 3
<211> LENGTH: 1074
<212> TYPE: DNA
<213> ORGANISM: Mus musculus

<400> SEQUENCE: 3

| | | | | | |
|---|---|---|---|---|---|
| atgaccaaat | catacagcga | gagcgggctg | atgggcgagc | ctcagcccca | aggtccccca | 60 |
| agctggacag | atgagtgtct | cagttctcag | gacgaggaac | acgaggcaga | caagaaagag | 120 |
| gacgagcttg | aagccatgaa | tgcagaggag | gactctctga | aaacgggggg | agaggaggag | 180 |
| gaggaagatg | aggatctaga | ggaagaggag | gaagaagaag | aggaggagga | ggatcaaaag | 240 |
| cccaagagac | ggggtcccaa | aaagaaaaag | atgaccaagg | cgcgcctaga | acgttttaaa | 300 |
| ttaaggcgca | tgaaggccaa | cgcccgcgag | cggaaccgca | tgcacgggct | gaacgcggcg | 360 |
| ctggacaacc | tgcgcaaggt | ggtaccttgc | tactccaaga | cccagaaact | gtctaaaata | 420 |
| gagacactgc | gcttggccaa | gaactacatc | tgggctctgt | cagagatcct | gcgctcaggc | 480 |
| aaaagccctg | atctggtctc | cttcgtacag | acgctctgca | aaggtttgtc | ccagcccact | 540 |
| accaatttgg | tcgccggctg | cctgcagctc | aaccctcgga | cttttcttgcc | tgagcagaac | 600 |
| ccggacatgc | ccccgcatct | gccaaccgcc | agcgcttcct | tcccggtgca | tcccactacc | 660 |
| taccagtccc | ctggactgcc | cagcccgccc | tacggcacca | tggacagctc | ccacgtcttc | 720 |
| cacgtcaagc | gccgccaca | cgcctacagc | gcagctctgg | agcccttctt | tgaaagcccc | 780 |
| ctaactgact | gcaccagccc | ttcctttgac | ggacccctca | gcccgccgct | cagcatcaat | 840 |
| ggcaacttct | ctttcaaaca | cgaaccatcc | gccgagtttg | aaaaaaatta | tgccttacc | 900 |
| atgcactacc | ctgcagcgac | gctggcaggg | ccccaaagcc | acggatcaat | cttctcttcc | 960 |
| ggtgccgctg | cccctcgctg | cgagatcccc | atagacaaca | ttatgtcttt | cgatagccat | 1020 |
| tcgcatcatg | agcgagtcat | gagtgcccag | cttaatgcca | tctttcacga | ttag | 1074 |

<210> SEQ ID NO 4
<211> LENGTH: 357
<212> TYPE: PRT
<213> ORGANISM: Mus musculus

<400> SEQUENCE: 4

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Glu Asp Glu
    50                  55                  60

Asp Leu Glu Glu Glu Glu Glu Glu Glu Glu Glu Glu Asp Gln Lys
65                  70                  75                  80

Pro Lys Arg Arg Gly Pro Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

```
Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145             150                 155                 160

Lys Ser Pro Asp Leu Val Ser Phe Val Gln Thr Leu Cys Lys Gly Leu
            165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
                260                 265                 270

Leu Ser Pro Pro Leu Ser Ile Asn Gly Asn Phe Ser Phe Lys His Glu
            275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

Phe Asp Ser His Ser His His Glu Arg Val Met Ser Ala Gln Leu Asn
            340                 345                 350

Ala Ile Phe His Asp
            355
```

METHODS AND COMPOSITIONS FOR TREATMENT OF DISEASE OR INJURY OF THE NERVOUS SYSTEM

REFERENCE TO RELATED APPLICATION

This application claims priority from U.S. Provisional Patent Application Ser. Nos. 61/673,471, filed Jul. 19, 2012 and 61/762,506, filed Feb. 8, 2013, the entire content of which is incorporated herein by reference.

GOVERNMENT SUPPORT

This invention was made with government support under Grant No. MH083911, awarded by the National Institutes of Health. The Government has certain rights in the invention.

FIELD OF THE INVENTION

General aspects of the invention relate to the in situ conversion of glial cells to functional neuronal cells in the central nervous system (CNS), and the methods to transforming glial cells to neuronal cells both in vitro and in vivo.

BACKGROUND OF THE INVENTION

The central nervous system in mammals is largely unable to regenerate itself following injury. Neurons are often killed or injured as a result of an injury or neurological condition, such as a disease or other pathology. It is well known that glial cells become reactive following brain or spinal cord injury, after a stroke or neurodegenerative diseases such as Alzheimer's disease. These reactive glial cells can proliferate and maintain a high number in the injury site, and eventually form a dense scar tissue called glial scar to prevent the growth of neurons.

Currently there is no method available to reverse glial scar for brain repair. There is an urgent need for methods of treatment of neurological conditions, particularly for generation of neurons in a subject having a neurological condition.

SUMMARY OF THE INVENTION

Methods of producing a neuronal phenotype in a glial cell are provided according to aspects of the present invention which include expressing exogenous NeuroD1 in the glial cell. The glial cell may be human or non-human, in vitro or in vivo.

Methods of producing a neuronal phenotype in a glial cell are provided according to aspects of the present invention which include expressing exogenous NeuroD1 in the glial cell, wherein expressing exogenous NeuroD1 includes delivering an expression vector including a nucleic acid encoding the exogenous NeuroD1 to the glial cell.

Methods of producing a neuronal phenotype in a glial cell are provided according to aspects of the present invention which include expressing exogenous NeuroD1 in the glial cell, wherein expressing exogenous NeuroD1 includes delivering a viral expression vector including a nucleic acid encoding the exogenous NeuroD1 to the glial cell.

Methods of producing a neuronal phenotype in a glial cell are provided according to aspects of the present invention which include expressing exogenous NeuroD1 in the glial cell, wherein expressing exogenous NeuroD1 includes delivering a retrovirus expression vector including a nucleic acid encoding the exogenous NeuroD1 to the glial cell.

The glial cell may be human or non-human mammalian, in vitro or in vivo. The glial cell may be a reactive astrocyte or NG2 cell.

Methods of producing a neuronal phenotype in a glial cell are provided according to aspects of the present invention which include expressing exogenous NeuroD1 in the glial cell, wherein the neuronal phenotype includes one or more of: neuronal morphology, expression of one or more neuronal markers, electrophysiologic characteristics of neurons, synapse formation and release of neurotransmitter.

Compositions provided according to aspects of the present invention are glial cells in vitro including exogenous NeuroD1.

Compositions provided according to aspects of the present invention are glial cells in vitro including an expression vector encoding NeuroD1.

Compositions provided according to aspects of the present invention are glial cells in vitro comprising exogenous NeuroD1, wherein the glial cells have a neuronal phenotype, wherein the neuronal phenotype includes one or more of: neuronal morphology, expression of one or more neuronal markers, electrophysiologic characteristics of neurons, synapse formation and release of neurotransmitter.

Compositions provided according to aspects of the present invention are glial cells in vitro including an expression vector encoding NeuroD1, wherein the glial cells have a neuronal phenotype, wherein the neuronal phenotype includes one or more of: neuronal morphology, expression of one or more neuronal markers, electrophysiologic characteristics of neurons, synapse formation and release of neurotransmitter.

Methods of treating a neurological condition in a subject in need thereof including administering a therapeutically effective dose of NeuroD1 to a glial cell of the subject; whereby exogenous NeuroD1 is expressed in the glial cell, producing a neuronal phenotype in the glial cell to ameliorate the neurological condition of the subject.

Methods of treating a neurological condition in a subject in need thereof including administering a therapeutically effective dose of NeuroD1 to a glial cell of the subject; whereby exogenous NeuroD1 is expressed in the glial cell, producing a neuronal phenotype in the glial cell to ameliorate the neurological condition of the subject, wherein the therapeutically effective dose of NeuroD1 is a therapeutically effective dose of a viral vector including a nucleic acid sequence encoding NeuroD1 protein.

Methods of treating a neurological condition in a subject in need thereof including administering a therapeutically effective dose of NeuroD1 to a glial cell of the subject; whereby exogenous NeuroD1 is expressed in the glial cell, producing a neuronal phenotype in the glial cell to ameliorate the neurological condition of the subject, wherein the therapeutically effective dose of NeuroD1 is a therapeutically effective dose of a viral vector including a nucleic acid sequence encoding NeuroD1 protein, wherein the nucleic acid sequence encoding NeuroD1 protein include a nucleic acid sequence selected from the group consisting of: a nucleic acid sequence encoding SEQ ID NO:2; a nucleic acid sequence encoding SEQ ID NO:4; SEQ ID NO:1; SEQ ID NO:3; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4.

According to aspects of methods of the present invention, a neurological condition in a subject in need of treatment is characterized by presence of reactive astrocytes.

According to aspects of methods of the present invention, a neurological condition in a subject in need of treatment is an injury to the central or peripheral nervous system.

According to aspects of methods of the present invention, a neurological condition in a subject in need of treatment is Alzheimer disease, Parkinson disease, amyotrophic lateral sclerosis or stroke.

Methods of treating a neurological condition in a subject in need thereof according to aspects of the present invention include providing a viral vector including a nucleic acid encoding NeuroD1; and delivering the viral vector to the central nervous system or peripheral nervous system of the subject, whereby the viral vector infects cells of the central nervous system or peripheral nervous system, respectively, producing infected cells and whereby exogenous NeuroD1 is expressed in the infected cells at a therapeutically effective level, wherein the expression of NeuroD1 in the infected cells results in a greater number of neurons in the subject compared to an untreated subject having the same neurological condition, whereby the neurological condition is treated.

BRIEF DESCRIPTION OF THE INVENTION

DETAILED DESCRIPTION OF THE INVENTION

Figure 1A:
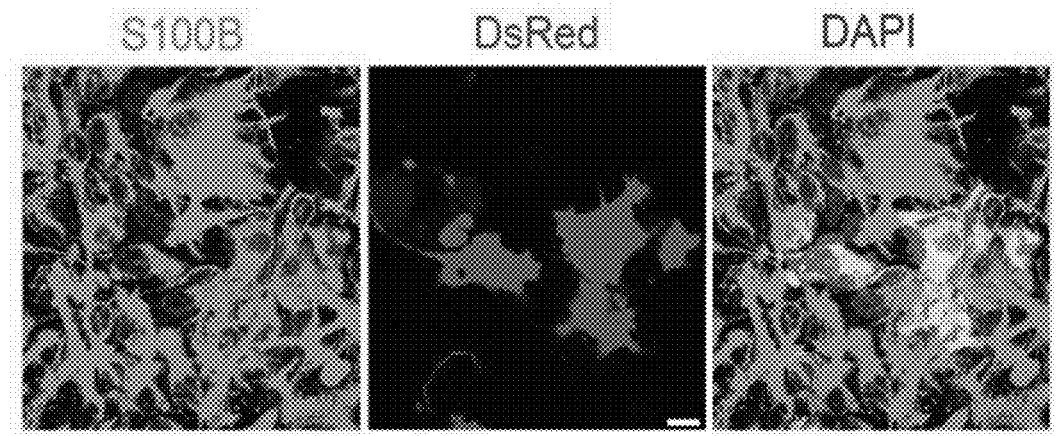
FIG. 1A shows that human astrocytes in culture were mostly immunopositive for S100β (an astrocyte marker) and infection with a control retrovirus expressing DsRed (pCAG-IRES-DsRed) showed no effect on their morphology and S100β expression.

Methods for producing new neurons in the brain in vivo are provided according to aspects of the present invention which include introducing NeuroD1 into a glial cell, particularly into a reactive astrocyte, microglial cell, or NG2 cell, thereby "converting" the reactive glial cell to a neuron.

Methods and compositions of the present invention have various uses, including for example, production of neurons in situ to treat a neurological condition of a subject.

Advantageously, in situ replacement of injured neuronal cells by conversion of endogenous reactive astrocytes into neurons eliminates the possibility of immunorejection such as can occur when a tissue/cell transplant is performed to replace damaged neuronal cells.

After brain/spinal cord injury or neurological disorders, glial cells such as astrocytes often over proliferate. Changing surplus glial cells into neurons will reduce the number of reactive glial cells, and in the meanwhile replenish lost neurons for internal brain repair.

Methods of producing a neuronal phenotype from a glial cell, such as an astrocyte or reactive astrocyte, are provided according to aspects of the present invention which include expressing exogenous NeuroD1 in the glial cell.

The glial cell, such as an astrocyte or reactive astrocyte, is in vitro or in vivo.

The glial cell, such as an astrocyte or reactive astrocyte, may be human or non-human mammalian, but can be non-mammalian as well.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Asubel, Ed., Short Protocols in Molecular Biology, Current Protocols; 5$^{th}$ Ed., 2002; B. Alberts et al., Molecular Biology of the Cell, 4$^{th}$ Ed., Garland, 2002; D. L. Nelson and M. M. Cox, Lehninger Principles of Biochemistry, 4$^{th}$ Ed., W.H. Freeman & Company, 2004; Engelke, D. R., RNA Interference (RNAi): Nuts and Bolts of RNAi Technology, DNA Press LLC, Eagleville, Pa., 2003; Herdewijn, p. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, Cold Spring Harbor Laboratory Press, 3$^{rd}$ Ed.; Dec. 15, 2002, ISBN-10:0879695919; Kursad Turksen (Ed.), Embryonic Stem Cells: Methods and Protocols in Methods in Molecular Biology, 2002; 185, Human Press: Current Protocols in Stem Cell Biology, ISBN: 9780470151808.

The singular terms "a," "an," and "the" are not intended to be limiting and include plural referents unless explicitly stated otherwise or the context clearly indicates otherwise.

The term "NeuroD1 protein" refers to a bHLH proneural transcription factor involved in embryonic brain development and in adult neurogenesis, see Cho, J. H. et al., Mol, Neurobiol., 30:35-47, 2004; Kuwabara, T. et al., Nature Neurosci., 12:1097-1105, 2009; and Gao, Z. et al., Nature Neurosci., 12:1090-1092, 2009. NeuroD1 is expressed late in development, mainly in the nervous system and is involved in neuronal differentiation, maturation and survival.

The term "NeuroD1 protein" encompasses human NeuroD1 protein, identified here as SEQ ID NO: 2 and mouse NeuroD1 protein, identified here as SEQ ID NO: 4. In addition to the NeuroD1 protein of SEQ ID NO: 2 and SEQ ID NO: 4, the term "NeuroD1 protein" encompasses variants of NeuroD1 protein, such as variants of SEQ ID NO: 2 and SEQ ID NO: 4, which may be included in methods of the present invention. As used herein, the term "variant" refers to naturally occurring genetic variations and recombinantly prepared variations, each of which contain one or more changes in its amino acid sequence compared to a reference NeuroD1 protein, such as SEQ ID NO: 2 or SEQ ID NO: 4. Such changes include those in which one or more amino acid residues have been modified by amino acid substitution, addition or deletion. The term "variant" encompasses orthologs of human NeuroD1, including for example mammalian and bird NeuroD1, such as, but not limited to NeuroD1 orthologs from a non-human primate, cat, dog, sheep, goat, horse, cow, pig, bird, poultry animal and rodent such as but not limited to mouse and rat. In a non-limiting example, mouse NeuroD1, exemplified herein as amino acid sequence SEQ ID NO: 4 is an ortholog of human NeuroD1.

Preferred variants have at least 75%, 80%, 85%, 90%, 91%, 92%, 93%, 94%, 95%, 96%, 97%, 98%, or 99% identity to SEQ ID NO: 2 or SEQ ID NO: 4.

Mutations can be introduced using standard molecular biology techniques, such as site-directed mutagenesis and PCR-mediated mutagenesis. One of skill in the art will recognize that one or more amino acid mutations can be introduced without altering the functional properties of the NeuroD1 protein. For example, one or more amino acid substitutions, additions, or deletions can be made without altering the functional properties of the NeuroD1 protein of SEQ ID NO: 2 or 4.

Conservative amino acid substitutions can be made in a NeuroD1 protein to produce a NeuroD1 protein variant. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

NeuroD1 variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

The term "NeuroD1 protein" encompasses fragments of the NeuroD1 protein, such as fragments of SEQ ID NOs. 2 and 4 and variants thereof, operable in methods and compositions of the present invention.

NeuroD1 proteins and nucleic acids may be isolated from natural sources, such as the brain of an organism or cells of a cell line which expresses NeuroD1. Alternatively, NeuroD1 protein or nucleic acid may be generated recombinantly, such as by expression using an expression construct, in vitro or in vivo. NeuroD1 proteins and nucleic acids may also be synthesized by well-known methods.

NeuroD1 included in methods and compositions of the present invention is preferably produced using recombinant nucleic acid technology. Recombinant NeuroD1 production includes introducing a recombinant expression vector encompassing a DNA sequence encoding NeuroD1 into a host cell.

A nucleic acid sequence encoding NeuroD1 introduced into a host cell to produce NeuroD1 according to embodiments of the invention encodes SEQ ID NO: 2, SEQ ID NO: 4, or a variant thereof. According to aspects of the present invention, the nucleic acid sequence identified herein as SEQ ID NO: 1 encodes SEQ ID NO: 2 and is included in an expression vector and expressed to produce NeuroD1. According to aspects of the present invention, the nucleic acid sequence identified herein as SEQ ID NO: 3 encodes SEQ ID NO: 4 and is included in an expression vector and expressed to produce NeuroD1.

It is appreciated that due to the degenerate nature of the genetic code, nucleic acid sequences substantially identical to SEQ ID NOs. 1 and 3 encode NeuroD1 and variants of NeuroD1, and that such alternate nucleic acids may be included in an expression vector and expressed to produce NeuroD1 and variants of NeuroD1. One of skill in the art will appreciate that a fragment of a nucleic acid encoding NeuroD1 protein can be used to produce a fragment of a NeuroD1 protein.

The term "expression vector" refers to a recombinant vehicle for introducing a nucleic acid encoding NeuroD1 into a host cell in vitro or in vivo where the nucleic acid is expressed to produce NeuroD1. In particular embodiments, an expression vector including SEQ ID NO: 1 or 3 or a substantially identical nucleic acid sequence is expressed to produce NeuroD1 in cells containing the expression vector. The term "recombinant" is used to indicate a nucleic acid construct in which two or more nucleic acids are linked and which are not found linked in nature. Expression vectors include, but are not limited to plasmids, viruses, BACs and YACs. Particular viral expression vectors illustratively include those derived from adenovirus, adeno-associated virus, retrovirus, and lentivirus.

An expression vector contains a nucleic acid that includes segment encoding a polypeptide of interest operably linked to one or more regulatory elements that provide for transcription of the segment encoding the polypeptide of interest. The term "operably linked" as used herein refers to a nucleic acid in functional relationship with a second nucleic acid. The term "operably linked" encompasses functional connection of two or more nucleic acid molecules, such as a nucleic acid to be transcribed and a regulatory element. The term "regulatory element" as used herein refers to a nucleotide sequence which controls some aspect of the expression of an operably linked nucleic acid. Exemplary regulatory elements include an enhancer, an internal ribosome entry site (IRES) or a 2A domain, an intron, an origin of replication, a polyadenylation signal (pA), a promoter, a transcription termination sequence, and an upstream regulatory domain, which contribute to the replication, transcription, post-transcriptional processing of an operably linked nucleic acid sequence. Those of ordinary skill in the art are capable of selecting and using these and other regulatory elements in an expression vector with no more than routine experimentation.

A nucleic acid sequence which is substantially identical to SEQ ID NO: 1 or 3 is characterized as having a complementary nucleic acid sequence capable of hybridizing to SEQ ID NO: 1 or 3 under high stringency hybridization conditions.

In addition to one or more nucleic acids encoding NeuroD1, one or more nucleic acid sequences encoding additional proteins can be included in an expression vector. For example, such additional proteins include non-NeuroD1 proteins such as reporters, including, but not limited to, beta-galactosidase, green fluorescent protein and antibiotic resistance reporters.

In particular embodiments, the recombinant expression vector encodes at least NeuroD1 of SEQ ID NO: 2, a protein having at least 95% identity to SEQ ID NO: 2, or a protein encoded by a nucleic acid sequence substantially identical to SEQ ID NO: 1.

In particular embodiments, the recombinant expression vector encodes at least NeuroD1 of SEQ ID NO: 4, a protein having at least 95% identity to SEQ ID NO: 4, or a protein encoded by a nucleic acid sequence substantially identical to SEQ ID NO: 2.

Optionally, a reporter gene is included in a recombinant expression vector encoding NeuroD1. A reporter gene may be included to produce a peptide or protein that serves as a surrogate marker for expression of NeuroD1 from the recombinant expression vector. The term "reporter gene" as used herein refers to gene that is easily detectable when expressed, for example by chemiluminescence, fluorescence, colorimetric reactions, antibody binding, inducible markers and/or ligand binding assays. Exemplary reporter genes include, but are not limited to, green fluorescent protein (GFP), enhanced green fluorescent protein (eGFP), yellow fluorescent protein (YFP), enhanced yellow fluorescent protein (eYFP), cyan fluorescent protein (CFP), enhanced cyan fluorescent protein (eCFP), blue fluorescent protein (BFP), enhanced blue fluorescent protein (eBFP), MmGFP (Zernicka-Goetz et al., Development, 124:1133-1137, 1997, dsRed, luciferase and beta-galactosidase (lacZ).

Expression of NeuroD1 using a recombinant expression vector is accomplished by introduction of the expression vector into a eukaryotic or prokaryotic host cell expression system such as an insect cell, mammalian cell, yeast cell, bacterial cell or any other single or multicellular organism recognized in the art. Host cells are optionally primary cells or immortalized derivative cells. Immortalized cells are those which can be maintained in-vitro for at least 5 replication passages.

Host cells containing the recombinant expression vector are maintained under conditions wherein NeuroD1 is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

According to aspects of the present invention, a recombinant expression vector including a nucleic acid encoding NeuroD1 is introduced into glial cells of a subject. Expression of exogenous NeuroD1 in the glial cells "converts" the glial cells into neurons.

According to aspects of the present invention, a recombinant expression vector including a nucleic acid encoding NeuroD1 is introduced into astrocytes of a subject. Expression of exogenous NeuroD1 in the glial cells "converts" the astrocytes into neurons.

According to aspects of the present invention, a recombinant expression vector including a nucleic acid encoding NeuroD1 is introduced into reactive astrocytes of a subject. Expression of exogenous NeuroD1 in the glial cells "converts" the reactive astrocytes into neurons.

Detection of expression of exogenous NeuroD1 following introduction of a recombinant expression vector including a nucleic acid encoding the exogenous NeuroD1 is accomplished using any of various standard methodologies including, but not limited to, detection of a reporter gene co-expressed with the exogenous NeuroD1.

The terms "converts" and "converted" are used herein to describe the effect of expression of NeuroD1 resulting in a change of a glial cell, astrocyte or reactive astrocyte phenotype to a neuronal phenotype. Similarly, the phrases "NeuroD1 converted neurons" and "converted neurons" are used herein to designate a cell including exogenous NeuroD1 protein which has consequent neuronal phenotype.

The term "phenotype" refers to well-known detectable characteristics of the cells referred to herein. The neuronal phenotype can be, but is not limited to, one or more of: neuronal morphology, expression of one or more neuronal markers, electrophysiological characteristics of neurons, synapse formation and release of neurotransmitter. For example, neuronal phenotype encompasses but is not limited to: characteristic morphological aspects of a neuron such as presence of dendrites, an axon and dendritic spines; characteristic neuronal protein expression and distribution, such as presence of synaptic proteins in synaptic puncta, presence of MAP2 in dendrites; and characteristic electrophysiological signs such as spontaneous and evoked synaptic events.

In a further example, glial phenotype such as astrocyte phenotype and reactive astrocyte phenotypes encompasses but is not limited to: characteristic morphological aspects of astrocytes and reactive astrocytes such as a generally "star-shaped" morphology; and characteristic astrocyte and reactive astrocyte protein expression, such as presence of glial fibrillary acidic protein (GFAP).

The term "NeuroD1 nucleic acid" refers to an isolated NeuroD1 nucleic acid molecule.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "NeuroD1 nucleic acid" encompasses isolated NeuroD1 nucleic acids having a sequence that has at least 70%, 75%, 80%, 85%, 90%, 91%, 92%, 93%, 94%, 95%, 96%, 97%, 98%, or 99% identity to the DNA sequence set forth in SEQ ID NO: 1 or SEQ ID NO: 3, or the complement thereof, or a fragment thereof, or an isolated DNA molecule having a sequence that hybridizes under high stringency hybridization conditions to the nucleic acid set forth as SEQ ID NO: 1 or SEQ ID NO: 3, a complement thereof or a fragment thereof. The nucleic acid of SEQ ID NO: 3 is an example of an isolated DNA molecule having a sequence that hybridizes under high stringency hybridization conditions to the nucleic acid set forth in SEQ ID NO: 1. A fragment of a NeuroD1 nucleic acid is any fragment of a NeuroD1 nucleic acid that is operable in aspects of the present invention including a NeuroD1 nucleic acid.

A nucleic acid probe or primer able to hybridize to a target NeuroD1 mRNA or cDNA can be used for detecting and/or quantifying mRNA or cDNA encoding NeuroD1 protein. A nucleic acid probe can be an oligonucleotide of at least 10, 15, 30, 50 or 100 nucleotides in length and sufficient to specifically hybridize under stringent conditions to NeuroD1 mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof.

The terms "complement" and "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID NO: 1 and SEQ ID NO: 3 will hybridize to the complement of substantially identical targets and not to unrelated sequences.

Methods of Treating a Neurological Condition

Methods of treating a neurological condition in a subject in need thereof are provided according to aspects of the present invention which include delivering a therapeutically effective amount of NeuroD1 to glial cells of the central nervous system or peripheral nervous system of the subject, the therapeutically effective amount of NeuroD1 in the glial cells results in a greater number of neurons in the subject compared to an untreated subject having the same neurological condition, whereby the neurological condition is treated.

The conversion of reactive glial cells into neurons also reduces neuroinflammation and neuroinhibitory factors associated with reactive glial cells, thereby making the glial scar tissue more permissive to neuronal growth so that neurological condition is alleviated.

The term "neurological condition" as used herein refers to any condition of the central and/or peripheral nervous system of a subject which is alleviated, ameliorated or prevented by additional neurons. Injuries or diseases which result in loss or inhibition of neurons and/or loss or inhibition of neuronal function are neurological conditions for treatment by methods according to aspects of the present invention.

Injuries or diseases which result in loss or inhibition of glutamatergic neurons and/or loss or inhibition of glutaminergic neuronal functions are neurological conditions for treatment by methods according to aspects of the present invention. Loss or inhibition of other types of neurons, such as GABAergic, cholinergic, dopaminergic, norepinephrinergic, or seratonergic neurons can be treated with the similar method.

Thus, for example, injuries or diseases which result in loss or inhibition of neurons and/or loss or inhibition of neuronal functions including, but not limited to, Alzheimer's disease, Parkinson disease, Amyotrophic lateral sclerosis (ALS), stroke, physical injury such as brain or spinal cord injury, and tumor, are neurological conditions for treatment by methods according to aspects of the present invention.

The term "therapeutically effective amount" as used herein is intended to mean an amount of an inventive composition which is effective to alleviate, ameliorate or prevent a symptom or sign of a neurological condition to be treated. In particular embodiments, a therapeutically effective amount is an amount which has a beneficial effect in a subject having signs and/or symptoms of a neurological condition.

The terms "treat," "treatment," and "treating" as used herein refer to alleviating, inhibiting or ameliorating a neurological condition, symptoms or signs of a neurological condition, and preventing symptoms or signs of a neurological condition, and include, but are not limited to therapeutic and/or prophylactic treatments.

Signs and symptoms of neurological conditions are well-known in the art along with methods of detection and assessment of such signs and symptoms.

Method of treating a neurological condition in a subject in need thereof are provided according to aspects of the present invention which include providing a viral vector comprising a nucleic acid encoding NeuroD1; and delivering the viral vector to the central nervous system or peripheral nervous system of the subject, whereby the viral vector infects glial cells of the central nervous system or peripheral nervous system, respectively, producing infected glial cells and whereby exogenous NeuroD1 is expressed in the infected glial cells at a therapeutically effective level, wherein the expression of NeuroD1 in the infected cells results in a greater number of neurons in the subject compared to an untreated subject having the same neurological condition, whereby the neurological condition is treated. In addition to the generation of new neurons, the number of reactive glial cells will also be reduced, resulting in less neuroinhibitory factors released, thereby making local environment more permissive to neuronal growth or axon penetration, hence alleviating neurological conditions.

Administration of a pharmaceutical composition to the central nervous system or peripheral nervous system of a subject is accomplished by methods including systemic or local administration.

According to aspects of the present invention, a viral vector comprising a nucleic acid encoding NeuroD1 is delivered by injection into the central nervous system or peripheral nervous system of a subject, such as by intracerebral injection, spinal cord injection and/or injection into the cerebrospinal fluid. Alternative viral delivery methods include but not limited to intravenous injection and intraperitoneal injection.

Combinations of therapies for a neurological condition of a subject are administered according to aspects of the present invention.

Embodiments of inventive compositions and methods are illustrated in examples shown and/or described herein. These examples are provided for illustrative purposes and are not considered limitations on the scope of inventive compositions and methods.

EXAMPLES

Example 1—Human Cortical Astrocytes

Human cortical astrocytes (HA1800) were purchased from ScienCell (California). Cells were subcultured when they were over 90% confluent. For subculture, cells were trypsinized by TrypLE™ Select (Invitrogen), centrifuged for 5 min at 1,000 rpm, re-suspended, and plated in a medium consisting of DMEM/F12 (Gibco), 10% fetal bovine serum (Gibco), penicillin/streptomycin (Gibco), 3.5 mM glucose (Sigma), and supplemented with B27 (Gibco), 10 ng/mL epidermal growth factor (EGF, Invitrogen), and 10 ng/mL fibroblast growth factor 2 (FGF2, Invitrogen). The astrocytes were cultured on poly-D-lysine (Sigma) coated coverslips (12 mm) at a density of 50,000 cells per coverslip in 24-well plates (BD Biosciences).

Example 2—Retrovirus Production

The pCAG-IRES-DsRed plasmid (Heinrich, C. et al., Directing astroglia from the cerebral cortex into subtype specific functional neurons. *PLoS Biol* 8 (5), e1000373 (2010)) containing the DsRed fluorescent reporter gene was used as the test plasmid. The mouse NeuroD1 gene was subcloned from the pAd NeuroD-1-nGFP (Addgene) and inserted into a pCAG-GFP-IRES-GFP retroviral vector (Zhao, C., Teng, E. M., Summers, R. G., Jr., Ming, G. L., & Gage, F. H., Distinct morphological stages of dentate granule neuron maturation in the adult mouse hippocampus. *J Neurosci* 26 (1), 3-11 (2006)) to generate the pCAG-NeuroD1-IRES-GFP plasmid, encoding the NeuroD1 protein of SEQ ID NO: 4. The restriction enzymes BamH I and Age I were used for subcloning. Viral particles were packaged in gpg helperfree HEK (Human embryonic kidney) cells to generate VSV-G (vesicular stomatitis virus glycoprotein)-pseudotyped retroviruses encoding neurogenic factors. The titers of viral particles were about $10^8$ particles/μl, determined after transduction of HEK cells. Each retrovirus only infects dividing cells such as proliferating astrocytes, but not non-dividing cells, such as neurons.

Example 3—Culture Conditions for Trans-Differentiation of Human Astrocytes into Neurons Twenty-four hours after infection of human cortical astrocytes with retrovirus encoding DsRed or encoding NeuroD1, the culture medium was completely replaced by a differentiation medium including DMEM/F12 (Gibco), 0.5% FBS (Gibco), 3.5 mM glucose (Sigma), penicillin/streptomycin (Gibco), and N2 supplement (Gibco). Brain-Derived Neurotrophic Factor (BDNF, 20 ng/mL, Invitrogen) was added to the cultures every four days during the differentiation to promote synaptic maturation.

Example 4—Animals for Mouse Model of Alzheimer Disease (AD)

In vivo experiments were conducted on wildtype C57BL6 and a 5xFAD transgenic mouse model of Alzheimer disease, referred to herein as "AD transgenic mice." The AD transgenic mice were purchased from The Jackson Laboratory (B6SJL-Tg (APPSwFlLon, PSEN1*M146L*L286V) 6799Vas/Mmjax, Oakley et al., J Neurosci. 2006 Oct. 4; 26(40):10129-40 and mated with C57BL6 mice. Mice were housed in a 12 hr light/dark cycle and supplied with enough food and water.

Example 5—Stereotaxic Virus Injection

Surgeries were performed on 1 month old WT mice, and on 5 month old littermates of WT and AD mice for virus injection. The mice were anesthesized by injecting 20 mL/kg 0.25% Avertin (a mixture of 25 mg/ml of Tribromoethylethanol and 25 μl/ml T-amyl-alcohol) into the peritoneum and then placed in a stereotaxic setup. Artificial eye ointment was applied to cover and protect the eye. The animals were operated with a midline scalp incision and a drilling hole on the skulls above somatosensory cortex. Each mouse received one injection (site: AP 1.25 mm, ML 1.4 mm, DV −1.5 mm) of either pCAG-IRES-DsRed retrovirus or pCAG-NeuroD1-IRES-GFP retrovirus with a 5 μl syringe and a 34 gauge needle. The injection volume and flow rate were controlled as 3 μl at 0.2 μl/min. In order to infect the whole surgery line in cortex, the needle was moved up during the injection at speed of 0.1 mm/min. After injection, the needle was kept for at least 5 additional minutes and then slowly withdrawn.

Example 6—Immunocytochemistry

For brain section staining, the mice were anesthesized with 0.25% Avertin and then sequentially perfused, first with saline solution (0.9% NaCl) to wash the blood and then with 4% paraformaldehyde (PFA) to fix the brain. The brains were removed and post fixed in 4% PFA overnight at 4° C., and then cut as about 45 μm sections by a vibratome (Leica). Coronal brain sections were first pretreated in 0.3% Triton X-100 in phosphate-buffered saline (PBS, pH 7.4) for 1 hour, followed by incubation in 3% normal goat serum, 2% normal donkey serum and 0.1% Triton X-100 in PBS for 1 hour.

For cell culture staining, the cultures were fixed in 4% PFA in PBS for 15 min at room temperature. Cells were first washed three times by PBS and then pretreated in 0.1%

Triton X-100 in PBS for 30 min, followed by incubation in 3% normal goat serum, 2% normal donkey serum and 0.1% Triton X-100 in PBS for 1 hour. Primary antibodies were incubated with either brain slices or cultures overnight at 4° C. in 3% normal goat serum, 2% normal donkey serum and 0.1% Triton X-100 in PBS. After additional washing in PBS, the samples were incubated with appropriate secondary antibodies conjugated to Alexa Fluor 488, Alexa 546, Alexa 647 (1:300, Molecular Probes), FITC, TRITC, or Dylight (1:500, Jackson ImmunoResearch) for 1 h at room temperature, followed by extensive washing in PBS. Coverslips were finally mounted onto a glass slide with an anti-fading mounting solution with DAPI (Invitrogen). Stainings were first examined with an epifluorescent microscope (Nikon TE-2000-S) and further analyzed with a confocal microscope (Olympus FV1000). Z-stacks of digital images, which can either release single confocal images or collapse as one resulting picture, were acquired and analyzed using FV10-ASW 3.0 Viewer software (Olympus).

The following primary antibodies were used: polyclonal anti-green fluorescent protein (GFP, chicken, 1:1000, Abcam, AB13970), polyclonal anti-Glial Fibrillary Acidic Protein (GFAP, rabbit, 1:500, Abcam, Z0334), polyclonal anti-Glial Fibrillary Acidic Protein (GFAP, chicken, 1:500, Millipore, AB5541), monoclonal anti-Red Fluorescent Protein (RFP, mouse, 1:300, CELL BIOLABS), polyclonal anti-Red Fluorescent Protein (RFP, rabbit, 1:2000, Rockland), polyclonal anti-vesicular glutamate transporter 1 (vGluT1, rabbit, 1:500, Synaptic Systems), polyclonal anti-vesicular glutamate transporter (SV2, rabbit, 1:2000, Developmental Studies Hybridoma Bank, Iowa City), polyclonal anti-Microtubule Associated Protein 2 (MAP2, Chicken, 1:1000, Abcam, AB5392), polyclonal anti-Microtubule Associated Protein 2 (MAP2, rabbit, 1:500, Chemicon, AB5622), monoclonal anti-SRY (sex determining region Y)-box 2 (Sox-2, mouse, 1:300, Abcam, AB79351), polyclonal anti-SRY (sex determining region Y)-box 2 (Sox-2, rabbit, 1:500, Millipore, AB5603), polyclonal anti-Glutamate decarboxylase (GAD1(GAD67), rabbit, 1:100, AnaSpec, 53501), monoclonal anti-βIII tubulin (Tuj1, mouse, 1:500, COVANCE, MMS-435P), polyclonal anti-musashi-1 (rabbit, 1:300, Neuromics, RA14128), polyclonal anti-Doublecortin (DCX, rabbit, 1:500, Abcam, AB18723), monoclonal anti-beta Amyloid (Aβ, mouse, 1:200, Abeam, AB11132), polyclonal anti-NeuN (rabbit, 1:500, Millipore, ABN78), monoclonal anti-NG2 (mouse, 1:200, Abeam, AB50009), polyclonal anti-Iba1 (goat, 1:200, Abcam, AB5076) and monoclonal anti-CNPase (mouse, 1:200, Abcam, AB6319).

Example 7—Cell Population Quantification and Statistical Analysis

For human and mouse converted neurons in vitro, cell counts were performed by taking images of several randomly chosen views per coverslip and analyzed by Image J software. For analyzing the cell populations in NeuroD1 or DsRed retrovirus-infected mouse brains, 10 to 14 views per section were randomly taken and the signals (GFP, DsRed, DCX, GFAP, Iba1, NG2 and CNPase) that co-localized with DAPI signal (nucleus staining) were quantified. Student's t test or followed with Bonferroni correction was used for statistical analysis.

Example 8—Patch-Clamp Recordings in Cell Cultures

For human astrocyte-converted neurons, whole-cell recordings were performed using the Multiclamp 700A patch-clamp amplifier (Molecular Devices, Palo Alto, Calif.) as described in Deng, L. et al., Sequential postsynaptic maturation governs the temporal order of GABAergic and glutamatergic synaptogenesis in rat embryonic cultures. *J Neurosci* 27 (40), 10860-10869 (2007). and the chamber was constantly perfused with a bath solution consisting of 128 mM NaCl, 30 mM glucose, 25 mM HEPES, 5 mM KCl, 2 mM $CaCl_2$, and 1 mM $MgCl_2$. The pH of bath solution was adjusted to 7.3 with NaOH, and osmolarity at 315-325 mOsm. Patch pipettes were pulled from borosilicate glass (4-5 MΩ) and filled with a pipette solution consisting of 147 mM KCl, 5 mM Na-phosphocreatine, 10 mM HEPES, 2 mM EGTA, 4 mM MgATP, and 0.5 mM $Na_2GTP$, pH 7.3 adjusted with KOH. The series resistance was typically 10-25 MΩ. For voltage-clamp experiments, the membrane potential was typically held at −70 or −80 mV. Drugs were applied through a gravity-driven drug delivery system (VC-6, Warner Hamden, Conn.). Data were acquired using pClamp 9 software (Molecular Devices, Palo Alto, Calif.), sampled at 10 kHz and filtered at 1 kHz. $Na^+$ and $K^+$ currents and action potentials were analyzed using pClamp 9 Clampfit software. Spontaneous synaptic events were analyzed using MiniAnalysis software (Synaptosoft, Decator, Ga.). All experiments were conducted at room temperature.

Example 9—Brain Slice Recordings

Cortical slices were prepared typically 1 month after virus injection and cut as 300 µm thick coronal slices with a Leica vibratome in ice cold cutting solution (containing 75 mM sucrose, 87 mM NaCl, 2.5 mM KCl, 0.5 mM $CaCl_2$, 7 mM $MgCl_2$, 25 mM $NaHCO_3$, 1.25 mM $NaH_2PO4$ and 20 mM glucose). Slices were maintained in artificial cerebral spinal fluid (ACSF) containing 119 mM NaCl, 2.5 mM KCl, 1.25 mM $NaH_2PO_4$, 26 mM $NaHCO_3$, 1.3 mM $MgCl_2$, 2.5 mM $CaCl_2$ and 10 mM glucose. Slices were incubated in ACSF, continuously bubbled with 95% $O_2$ and 5% $CO_2$, first at 34° C. for 30 minutes, and then at room temperature. Whole-cell recordings were performed using a pipette solution containing 147 mM KCl, 5 mM Na-phosphocreatine, 10 mM HEPES, 2 mM EGTA, 4 mM MgATP, and 0.5 mM $Na_2GTP$ (pH 7.3 adjusted with KOH, 290 mOsm/L). Pipette resistance was 3-4 MΩ, and series resistance was typically 20-40 MΩ. The holding potential for voltage-clamp experiments was −70 or −80 mV. Data were collected using pClamp 9 software (Molecular Devices, Palo Alto, Calif.), sampled at 10 kHz and filtered at 1 kHz, analyzed with Clampfit and Synaptosoft softwares.

Example 10—Effect of Expression of Exogenous NeuroD1 in Astrocytes

Cultures of human cortical astrocytes (SciCell, California) were infected with retrovirus encoding NeuroD1, pCAG-NeuroD1-IRES-GFP or control retrovirus pCAG-IRES-DsRed, described in Example 2. FIGS. 1, 2 and 3 show results of these infections.

FIG. 1 shows direct conversion of human astrocytes into neurons by expression of exogenous NeuroD1 in the cells. The human astrocytes in culture were mostly immunopositive for S100β (an astrocyte marker) and infection with a control retrovirus expressing DsRed (pCAG-IRES-DsRed) showed no effect on their morphology and S100β expression, FIG. 1A. Scale bar, 20 µm.

Figure 1B:
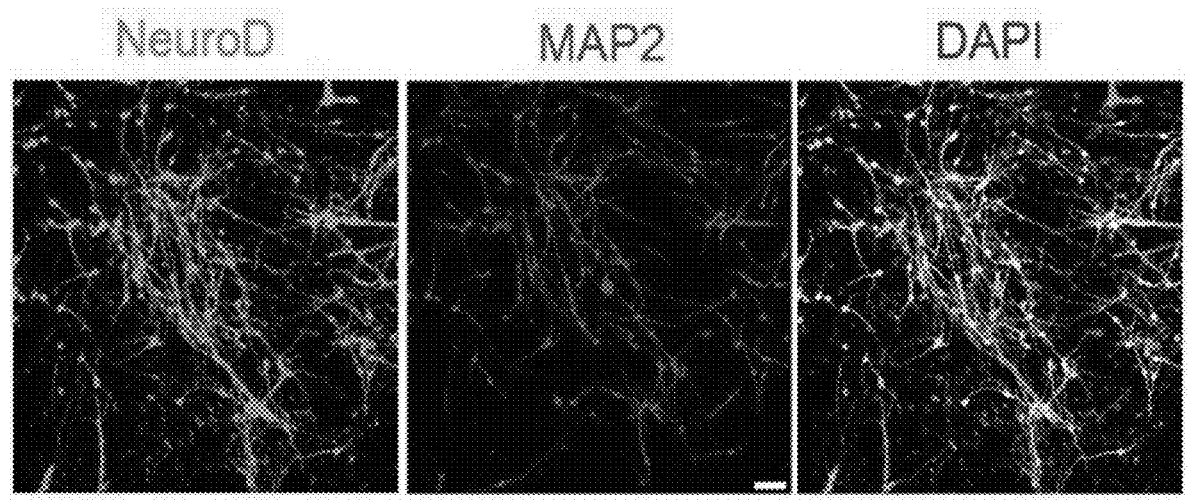
FIG. 1B shows NeuroD1-IRES-GFP infected human astrocytes at 30 DPI converted into MAP2-positive neurons.
Figure 2:
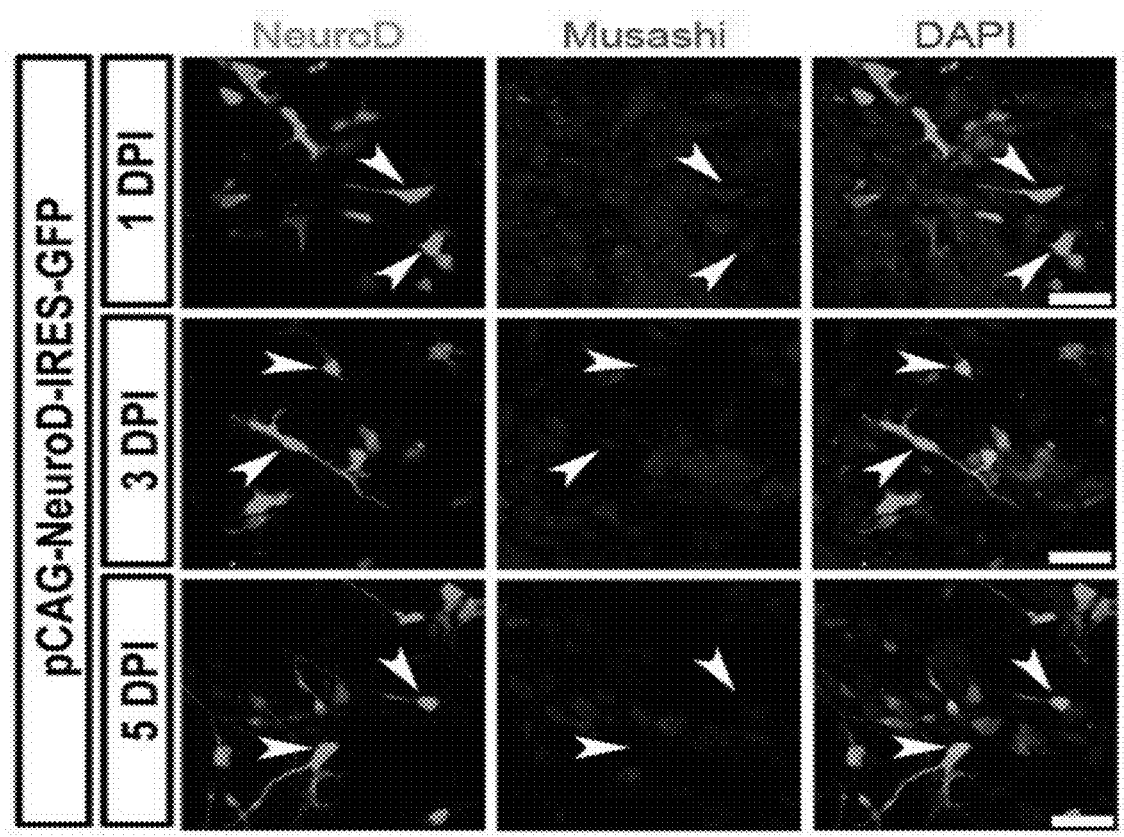
FIG. 2 shows no intermediate neuroprogenitor stage during human astrocyte-neuron conversion.

However, infection by NeuroD1 significantly changed the cell morphology, and the majority of pCAG-NeuroD1-IRES-GFP infected cells became immunopositive for a neuronal marker MAP2, FIG. 1B, scale bar, 20 µm. FIG. 1B shows NeuroD1-IRES-GFP infected human astrocytes at 30 DPI converted into MAP2-positive neurons.

Figure 1C:
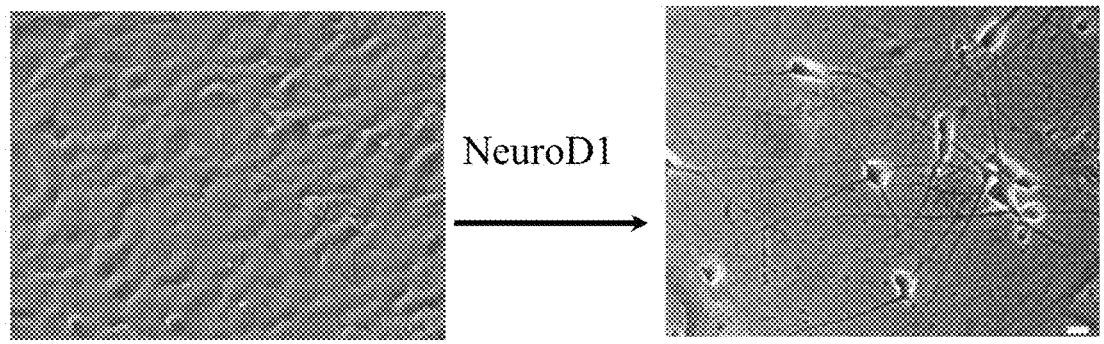
FIG. 1C shows phase images showing NeuroD1-induced morphological change from astrocytes (left) to neurons (right) at 45 DPI.

The phase contrast images in FIG. 1C, scale bar, 20 µm, illustrate the dramatic morphological change from astrocytes to neurons after NeuroD1 infection. FIG. 1C shows phase images showing NeuroD1-induced morphological change from astrocytes (left) to neurons (right) at 45 DPI.

Figure 1D:
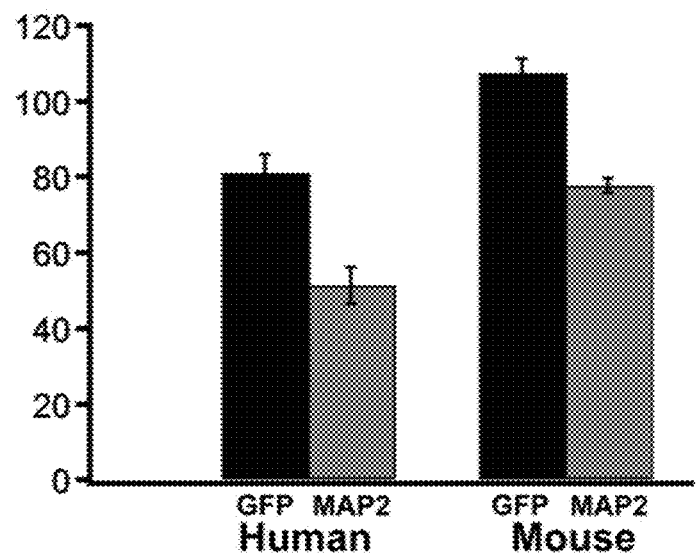
FIG. 1D shows quantification of total number of cells infected by NeuroD1-IRES-GFP and the number of MAP2-positive neurons after NeuroD1-induced conversion (30 DPI) in both human and mouse astrocytes.

FIG. 1D shows quantification of total number of cells infected by NeuroD1-IRES-GFP (per image field taken with 20× lens, as shown in B) and the number of MAP2-positive neurons after NeuroD1-induced conversion (30 DPI) in both human and mouse astrocytes. NeuroD1 efficiently converted both human and mouse astrocytes into neurons as shown in FIG. 1D. Quantitatively, among all NeuroD1-infected human astrocytes (n=1640 with 4 independent repeats), about 63.0±0.1% was converted into neurons, FIG. 1D.

Figure 1E:
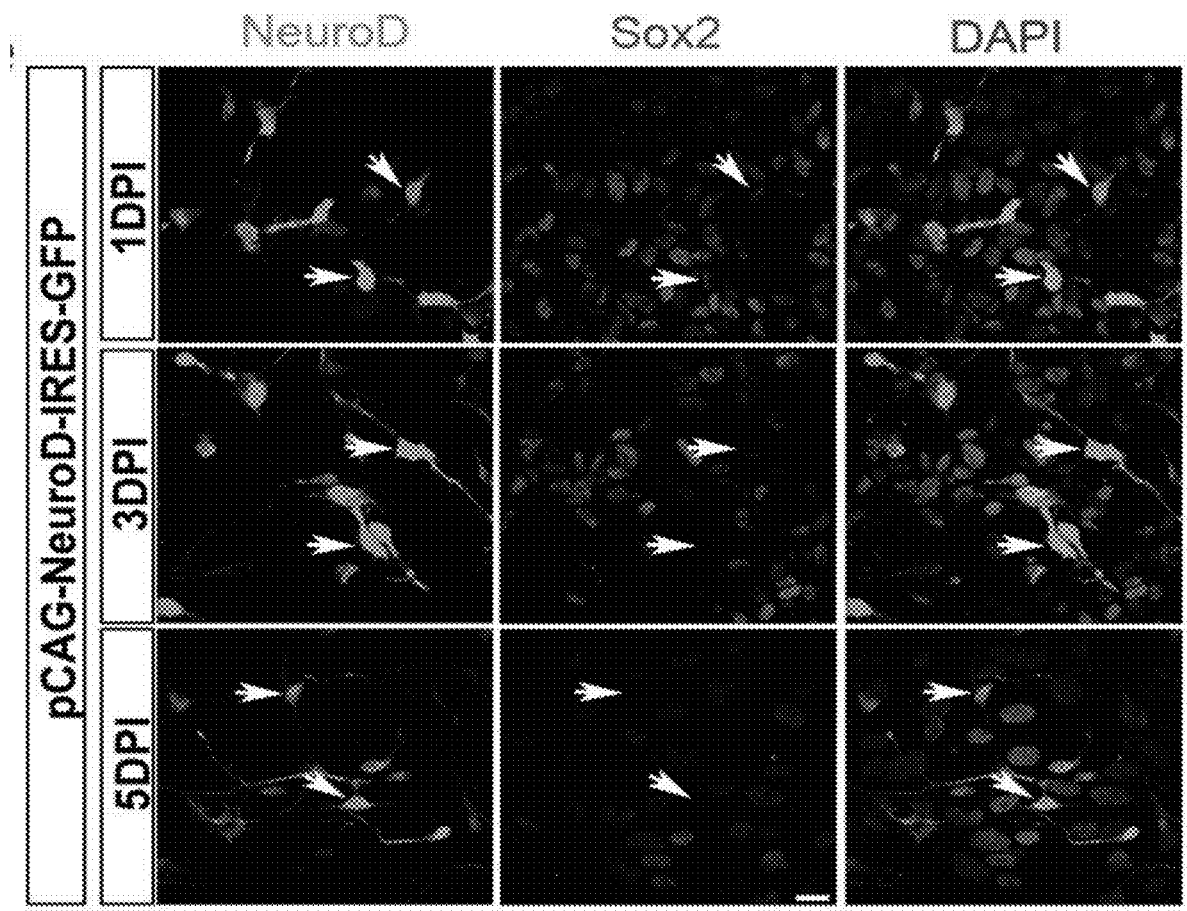
FIG. 1E shows direct conversion of human astrocytes into neurons by NeuroD1 without transition through the Sox2-positive neuroprogenitor stage.

To investigate whether NeuroD1-induced conversion has a transient neuroprogenitor stage, the trans-differentiation process was monitored from 24 hours till 5 days after NeuroD1 infection of human astrocytes (FIG. 1E, Scale bar, 20 µm). FIG. 1E, shows direct conversion of human astrocytes into neurons by NeuroD1 without transition through the Sox2-positive neuroprogenitor stage. Note that astrocytes usually had low level of Sox2 expression but NeuroD1-infected astrocytes (arrows) were devoid of Sox2 signal. DAPI staining of the cell nucleus shows the total number of cells in the imaging field.

FIG. 2 shows no intermediate neuroprogenitor stage during human astrocyte-neuron conversion. NeuroD1-infected cells (FIG. 2, left, arrowheads) did not show any increase in the expression of neural stem cell marker Musashi (middle) over 1, 3 and 5 DPI. Scale bar, 40 µm.

No transient increase in the expression level of neural stem cell marker Sox2 (FIG. 1E) or Musashi (FIG. 2) occurred during the early conversion period. Note that after only 1-3 days post infection (DPI) with NeuroD1, some astrocytes already became neuron-like cells with clearly extended neurites (FIG. 1E, arrows). Similar effects are expected by expression of exogenous human NeuroD1. Therefore, human astrocytes are directly converted into neurons by exogenous NeuroD1 expression.

FIGS. 3A-F show that the NeuroD1-converted human neurons are functionally connected.

Figure 3A:
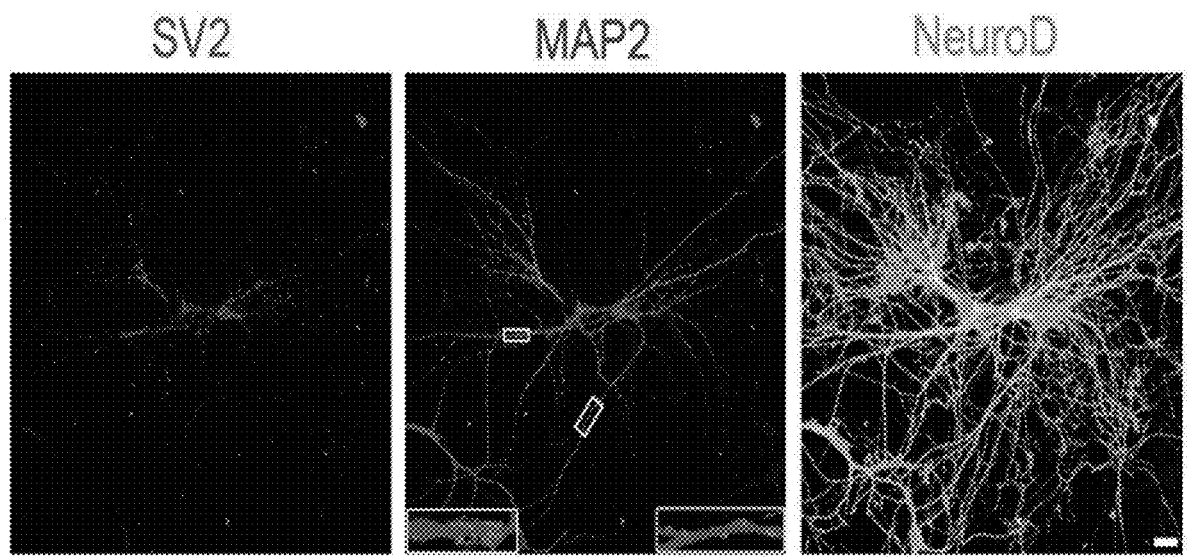
FIG. 3A shows synaptic puncta (SV2, left) on the dendrites (MAP2, middle) of NeuroD1-converted human neurons (45 DPI, right)

Immunostaining with synaptic marker SV2 and glutaminergic synaptic marker VGluT1 was performed to show that NeuroD1-converted neurons are functionally connected (FIG. 3A). After NeuroD1-induced conversion (45 DPI), numerous SV2 puncta on MAP2-labeled neuronal dendrites (FIG. 3A) were observed. FIG. 3A, scale bar, 20 µm, shows synaptic puncta (SV2, left) on the dendrites (MAP2, middle) of NeuroD1-converted human neurons (45 DPI, right).

Figure 3B:
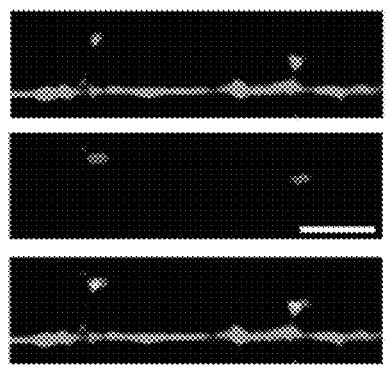
FIG. 3B is a high magnification image showing vGlut1 puncta (vesicular glutamate transporter 1, middle) co-localized with dendritic spines on NeuroD1-converted neurons, bottom.

Some neurons even showed mushroom-like mature spines, which were co-localized with VGluT1 puncta. FIG. 3B, scale bar, 10 µm, is a high magnification image showing vGlut1 puncta (vesicular glutamate transporter 1, middle) co-localized with dendritic spines on NeuroD1-converted neurons.

Figure 3C:
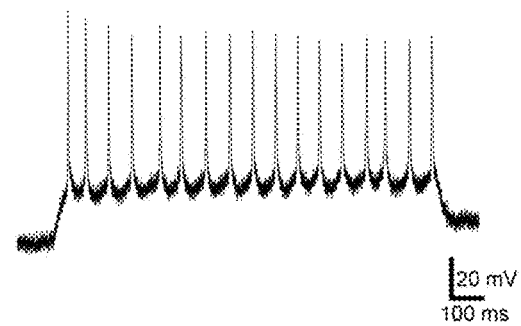
FIG. 3C shows representative trace of repetitive action potentials in NeuroD1-converted neurons (20 DPI)
Figure 3D:
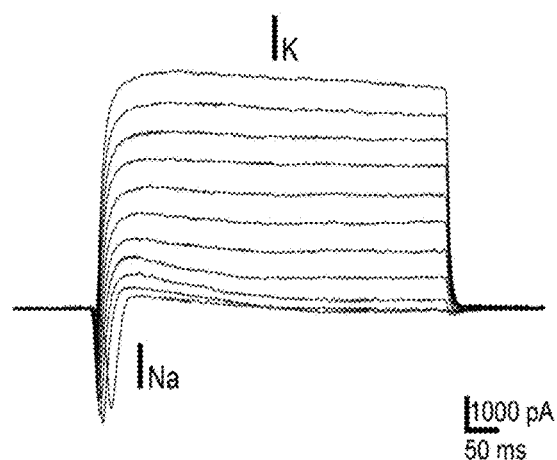
FIG. 3D shows the $Na^+$ and $K^+$ currents recorded from NeuroD1-converted neurons (30 DPI).

Patch clamp recordings were employed to test the functionality of converted human neurons. After 20 DPI, repetitive action potential firing (FIG. 3C), and large sodium ($I_{Na}$) and potassium currents ($I_K$) (FIG. 3D) were recorded. FIG. 3C shows representative trace of repetitive action potentials in NeuroD1-converted neurons (20 DPI). FIG. 3D shows the Na$^+$ and K$^+$ currents recorded from NeuroD1-converted neurons (30 DPI).

Figure 3E:
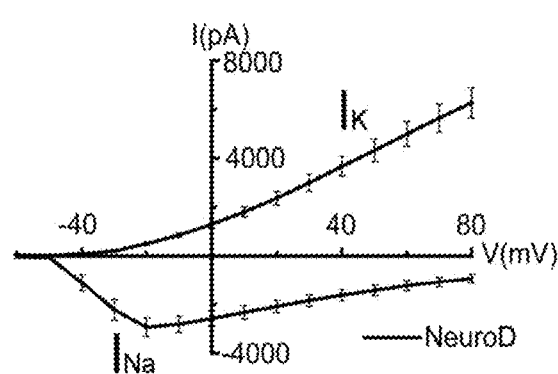
FIG. 3E shows the I-V curves of $Na^+$ and $K^+$ currents in NeuroD1-converted neurons (30 DPI)

FIG. 3E illustrates the I-V curves for $I_{Na}$ (peak amplitude at −20 mV, 2927±378 pA, n=12) and $I_K$ (peak amplitude at +80 mV, 6267±617 pA, n=12) in NeuroD1-converted neurons. FIG. 3E shows the I-V curves of Na$^+$ and K$^+$ currents in NeuroD1-converted neurons (30 DPI). The membrane potential was held at −80 mV and depolarized from −60 mV to +80 mV.

Figure 3F:
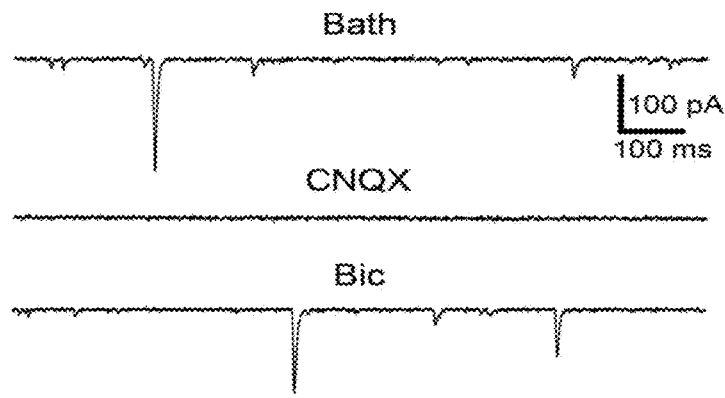
FIG. 3F shows representative traces of spontaneous synaptic events in NeuroD1-converted neurons (40 DPI)

Functional synaptic events were recorded in NeuroD1-converted neurons (frequency=1.6±0.3 Hz, and amplitude=23.2±0.8 pA, n=15), which were completely blocked by AMPA/kainate receptor antagonist CNQX (10 µM) but not by GABA$_A$ receptor antagonist bicuculline (20 µM), FIG. 3F. FIG. 3F shows representative traces of spontaneous synaptic events in NeuroD1-converted neurons (40 DPI). Note that all events were blocked by CNQX (10 µM) but not Bic (20 µM), suggesting that they were glutamatergic events.

Thus, NeuroD1 converts human astrocytes into functional glutamatergic neurons.

Example 11—Effect of Expression of Exogenous NeuroD1 in Astrocytes In Vivo

FIGS. 4A-H and 5A-D show in vivo conversion of reactive astrocytes into functional neurons after brain injury.

In the adult mouse cortex, astrocytes are typically quiescent unless activated by injury or diseases. An in vivo mouse model is used in this example to examine the therapeutic potential of reactive astrocytes induced by brain injury, when these are converted into functional neurons.

Figure 4A:
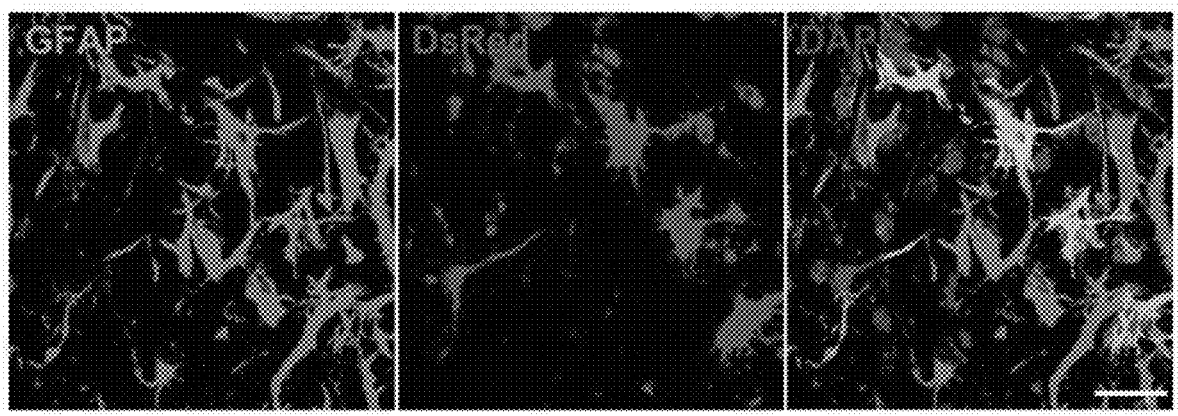
FIG. 4A shows GFAP-labeled reactive astrocytes at the injury site after injecting control retrovirus expressing DsRed in mouse cortex.
Figure 5A:
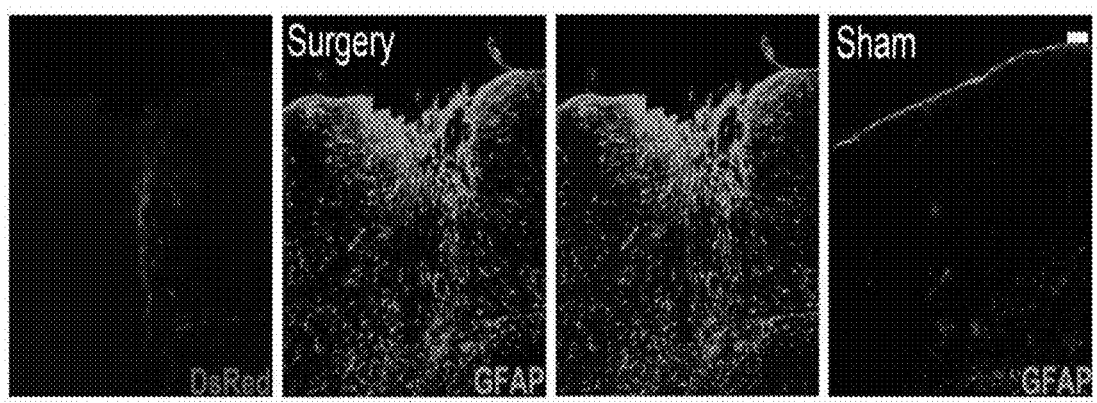
FIG. 5A shows low magnification images showing many reactive astrocytes (GFAP) in the injection area (surgery side) after injecting DsRed retrovirus in the WT mouse cortex (1 month old); and non-surgery side (sham) had only a few GFAP-labeled astrocytes.
Figure 5B:
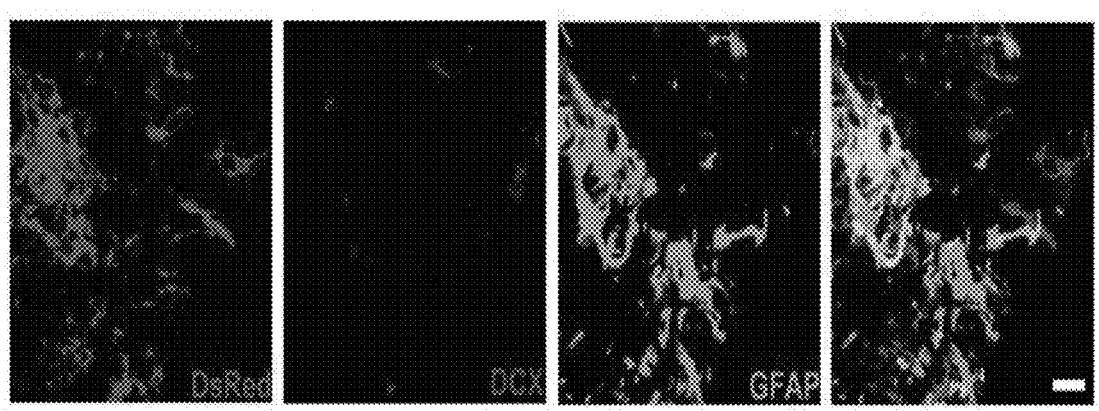
FIG. 5B shows high magnification images showing some DsRed-infected cells (14 DPI) were positive for GFAP but rarely labeled by DCX.

A brain injury model, where reactive astrocytes were induced by stab lesion during stereotaxic injection of retrovirus into mouse somatosensory cortex, was employed. Either pCAG-IRES-DsRed retrovirus or pCAG-GFP-IRES-GFP retrovirus was injected as described in Example 5. The retrovirus only infects dividing cells such as reactive astrocytes, but not endogenous neurons, providing beneficial effects. As expected, injecting the control virus pCAG-IRES-DsRed expressing DsRed in mouse cortex revealed many GFAP-positive reactive astrocytes in the vicinity of injury site, FIG. 4A and FIGS. 5A-B. FIG. 4A and FIGS. 5A-B show GFAP-labeled reactive astrocytes at the injury site after injecting control retrovirus expressing DsRed in mouse cortex (14 DPI). Scale bar, 20 µm for 4A. FIG. 5A shows a low magnification image showing many reactive astrocytes (GFAP) in the injection area (surgery side) after injecting DsRed retrovirus in the WT mouse cortex (1 month old). Non-surgery side (sham) had only a few GFAP-labeled astrocytes, scale bar, 100 µm. FIG. 5B shows high magnification images showing some DsRed-infected cells (14 DPI) were positive for GFAP but rarely labeled by DCX, scale bar, 10 µm.

Figure 4B:
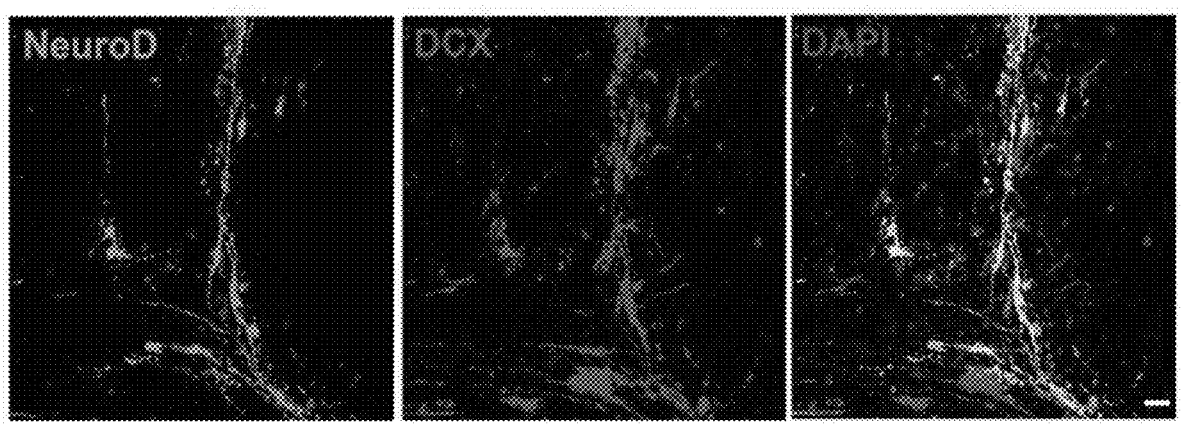
FIG. 4B shows NeuroD1-IRES-GFP infected cells were immunopositive for DCX along the injection site (14 DPI)
Figure 4C:
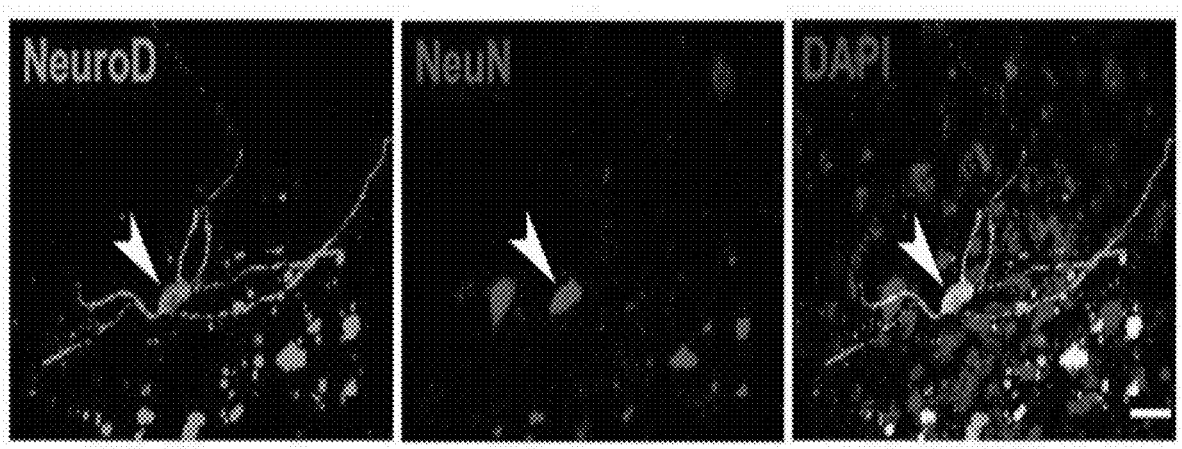
FIG. 4C shows NeuroD1-IRES-GFP infected cells were also immunopositive for NeuN and extended long neurites (21 DPI)
Figure 5C:
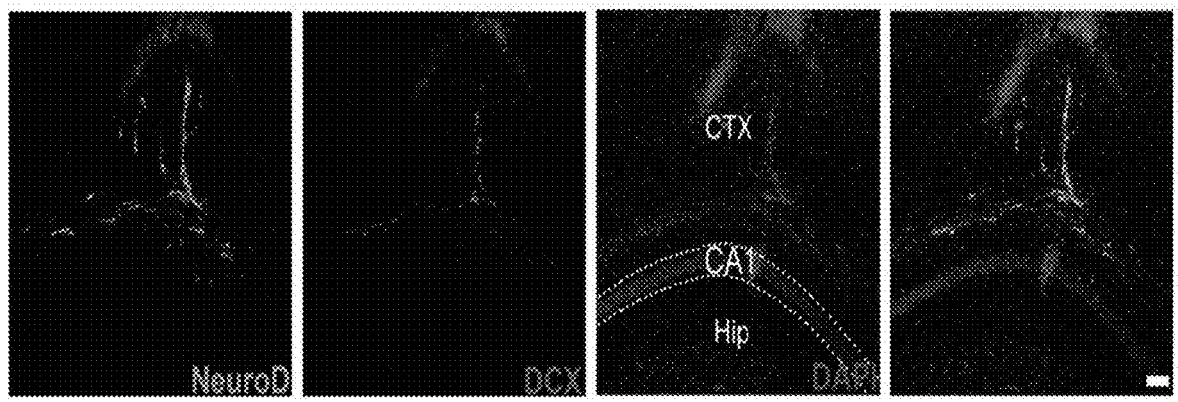
FIG. 5C shows low magnification images showing NeuroD1-infected cells (14 DPI) positive for DCX in cortical area and above hippocampal area.
Figure 5D:
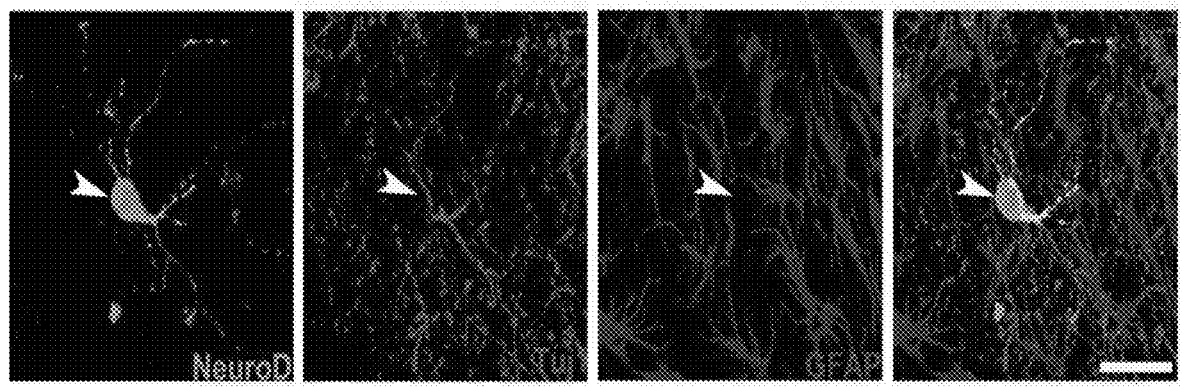
FIG. 5D shows a high magnification image showing an NeuroD1-transduced cell immunopositive for Tuj1 but not GFAP.

After injecting retrovirus expressing NeuroD1-IRES-GFP, many NeuroD1-infected cells along the injection site were immunopositive for neuronal markers doublecortin (DCX), neuronal nuclei (NeuN), or β3-tubulin (Tuj1), and showed extensive neurites, FIGS. 4B-C and FIG. 5C-D. FIG. 4B shows NeuroD1-IRES-GFP infected cells were immunopositive for DCX along the injection site (14 DPI). FIG. 4C, NeuroD1-IRES-GFP infected cells were also immunopositive for NeuN and extended long neurites (21 DPI). Scale bar, 20 µm for 4B-C. The total number of NeuroD1-transduced neurons after single injection in the cortex is quantified and 175±13 neurons were found around the injection site (14 DPI, n=3 animals, 6-8 sections for each mouse brain). FIG. 5C shows low magnification images showing NeuroD1-infected cells (14 DPI) positive for DCX in cortical area and above hippocampal area, scale bar, 100 μM. FIG. 5D shows a high magnification image showing a NeuroD1-transduced cell immunopositive for Tuj1 but not GFAP, scale bar, 20 μm.

Figure 4D:
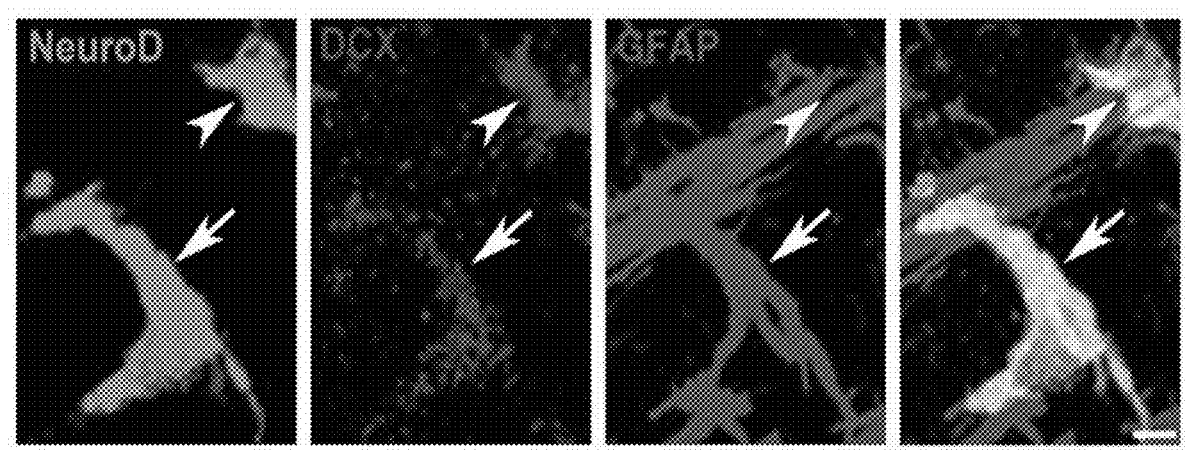
FIG. 4D shows transitional stage between GFAP-positive astrocytes and DCX-labeled neurons revealed 3 days after injecting NeuroD1 retrovirus, the arrow points to a NeuroD1-infected cell with substantial GFAP signal and weak DCX signal, whereas the arrowhead points to a NeuroD1-infected cell mainly stained by DCX but little GFAP signal.

To investigate whether NeuroD1-transduced neurons were converted from reactive astrocytes, NeuroD1-transduced cortical tissue was immunostained with GFAP and DCX at 2-3 DPI in an attempt to capture a possible transitional stage. During this early expression period, a mixture of NeuroD1-infected cells that were labeled by either DCX or GFAP was observed. Surprisingly, some NeuroD1-infected cells were even labeled by both GFAP and DCX, suggesting that these cells were transitioning from astrocytes into neurons, FIG. 4D, arrow. FIG. 4D shows transitional stage between GFAP-positive astrocytes and DCX-labeled neurons revealed 3 days after injecting NeuroD1 retrovirus. The arrow points to a NeuroD1-infected cell with substantial GFAP signal and weak DCX signal, whereas the arrowhead points to a NeuroD1-infected cell mainly stained by DCX but little GFAP signal. Scale bar, 5 μm.

Figure 4E:
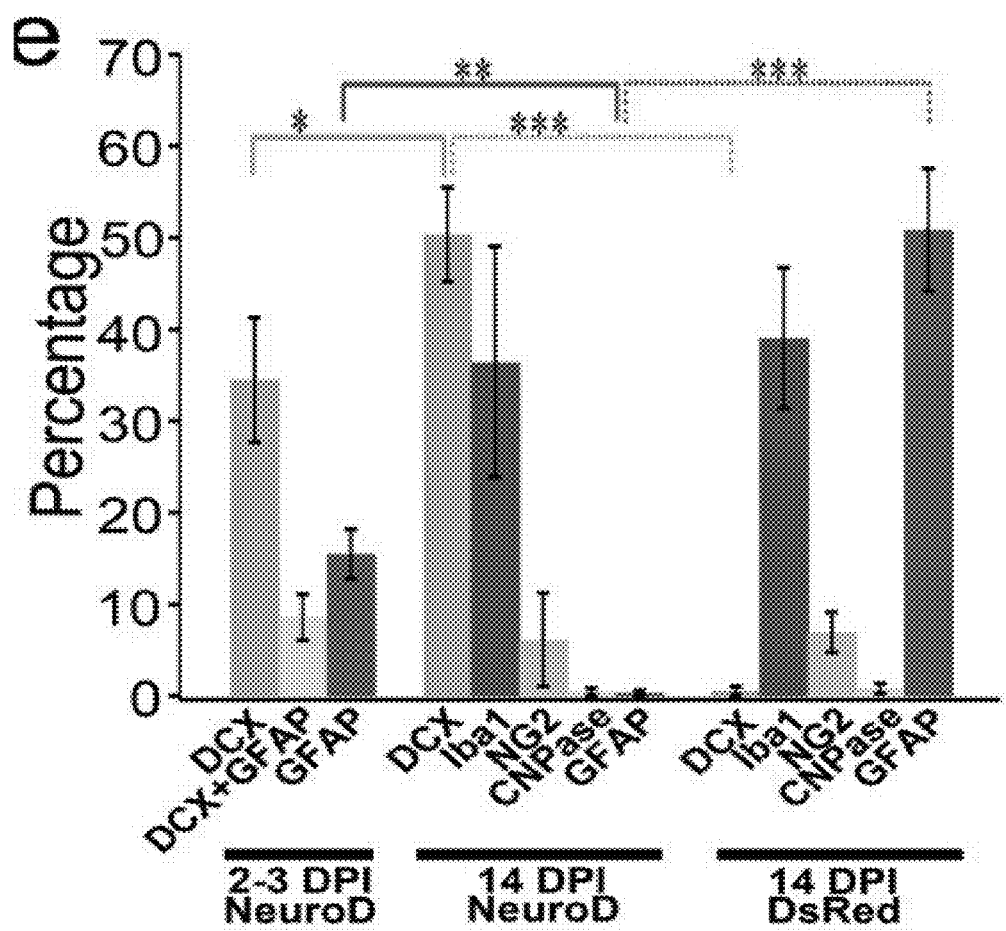
FIG. 4E shows quantification of the percentage of cells immunopositive for DCX, GFAP, Iba1, NG2, and CNPase among NeuroD1- or DsRed-infected cell populations.

Quantitatively, after 2-3 DPI, NeuroD1-infected cells had 15.5±2.7% GFAP positive, 34.5±6.8% DCX positive, and 8.6±2.5% immunopositive for both GFAP and DCX, FIG. 4E. After 14 DPI, NeuroD1-infected cells were rarely positive for GFAP (0.31±0.27%), but the percentage of DCX-positive neurons significantly increased (50.3±5.1%), suggesting that most of the NeuroD1-infected reactive astrocytes have been converted into neurons after 2 weeks, FIG. 4E.

Figure 6A:
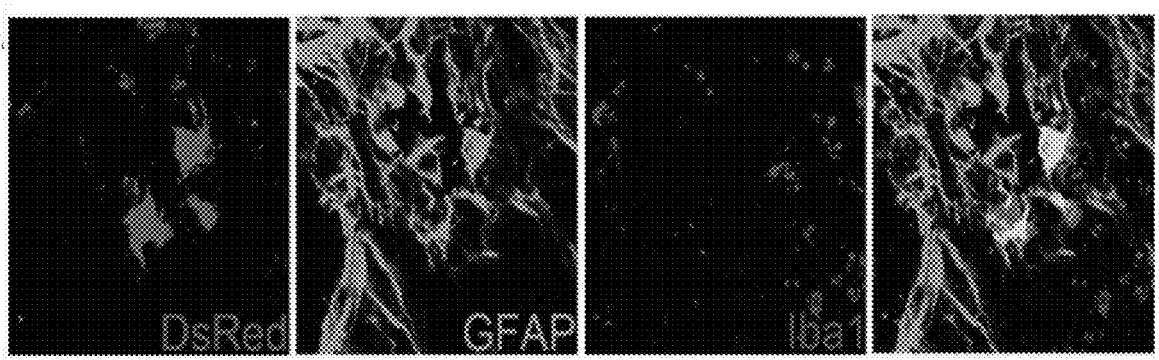
FIGS. 6A-6F show different glial cell types infected by retrovirus in the mouse cortex.
Figure 6B:
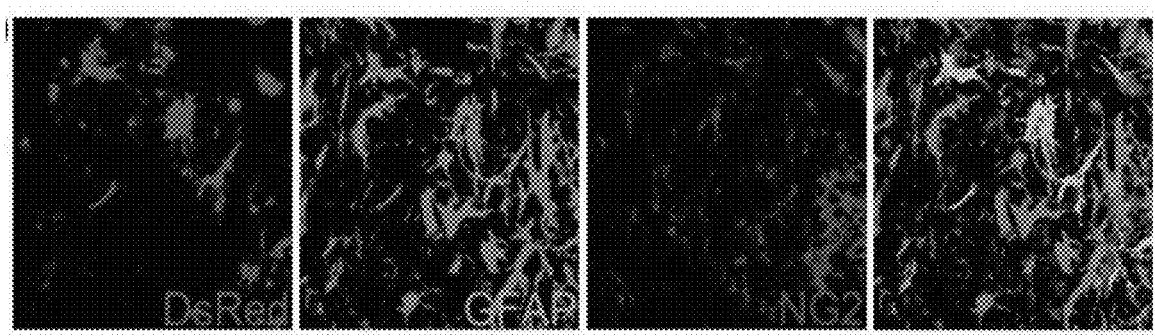
Figure 6C:
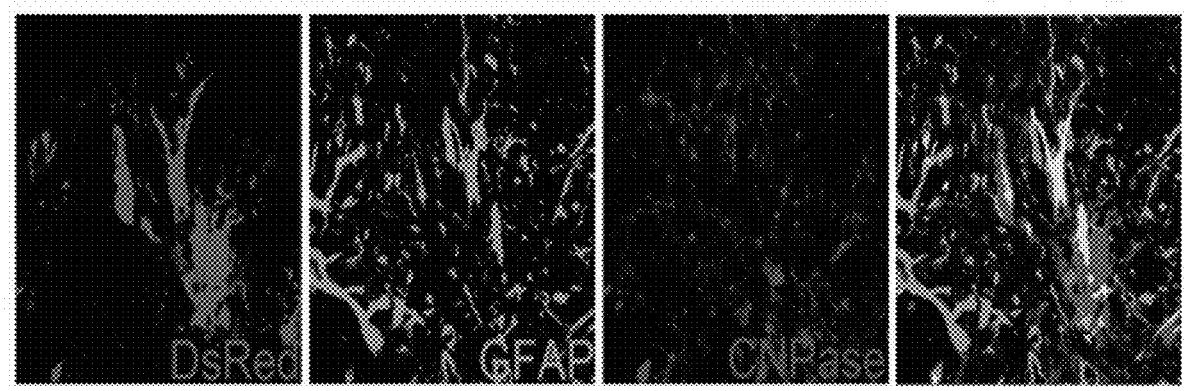
Figure 6D:
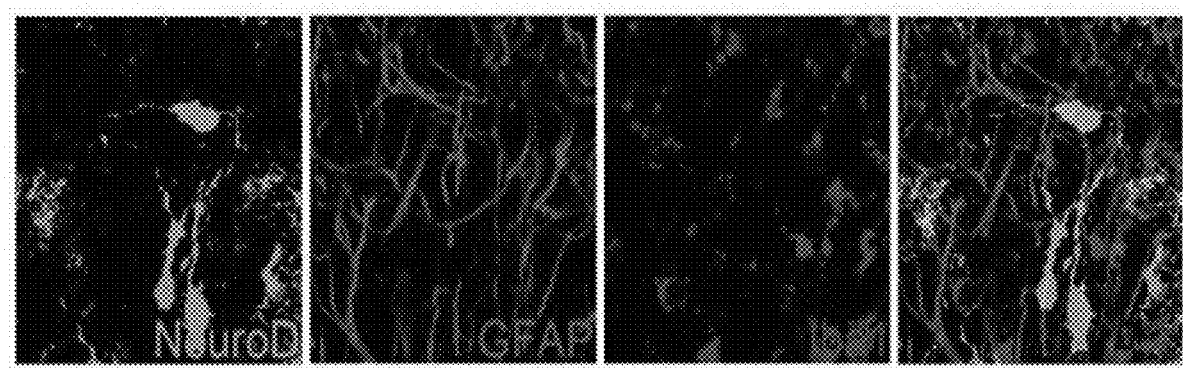
Figure 6E:
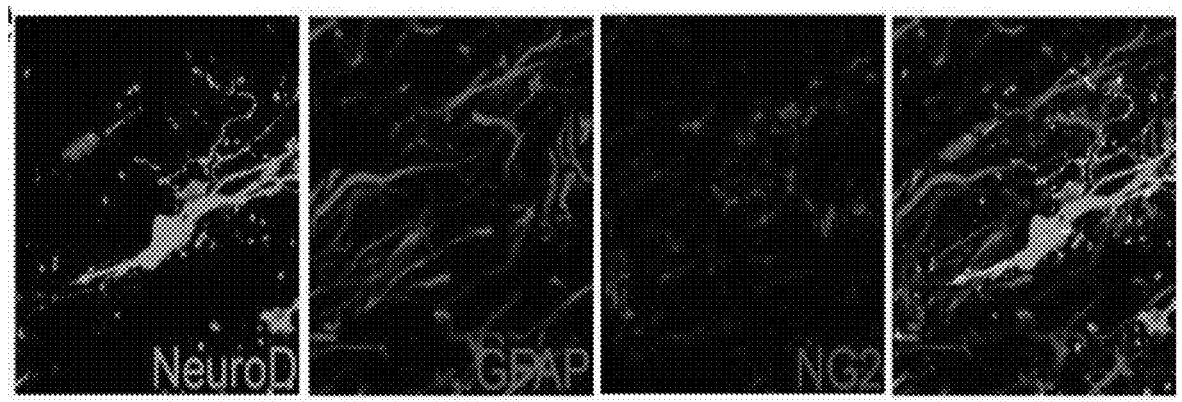
Figure 6F:
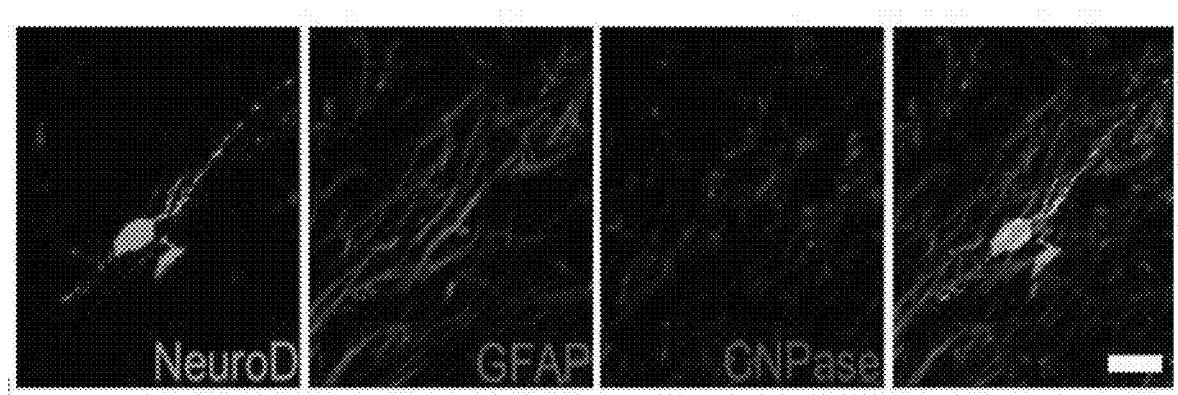
Figure 6G:
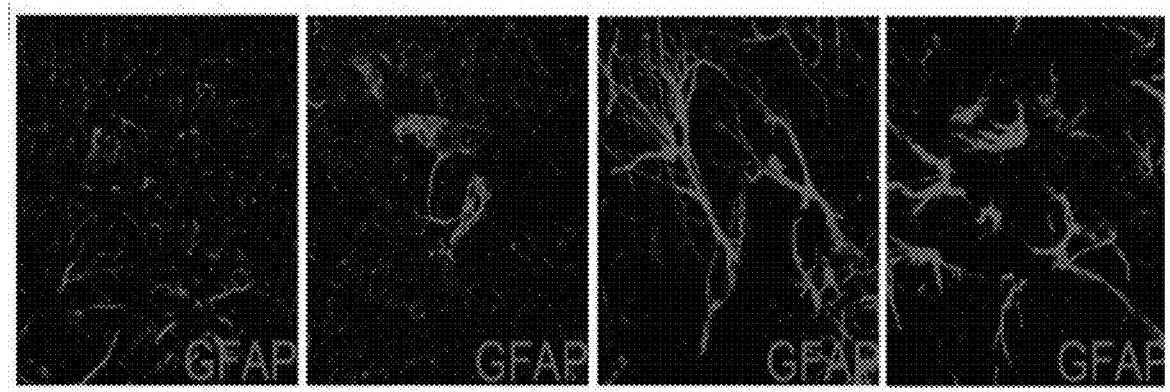
FIG. 6G shows GFAP expression.

FIG. 4E shows quantification of the percentage of cells immunopositive for DCX, GFAP, Iba1, NG2, and CNPase among NeuroD1- or DsRed-infected cell populations. Note that the majority of NeuroD1-infected cells (14 DPI) were DCX positive, whereas most of the DsRed-infected cells were GFAP positive. n=5 animals for NeuroD1 infection at 14 DPI and 2 animals at 2-3 DPI; and 4 animals for DsRed infection (14 DPI). The rest of NeuroD1-infected cells were microglia (Iba1 staining, 36.5±12.6%) and NG2 cells (NG2 staining, 6.1±5.1%), but rarely oligodendrocytes (CNPase staining, 0.45±0.39%), FIG. 6. For control experiments, it was found that half of the DsRed-infected cells (14 DPI) were astrocytes (50.8±6.7%) instead of neurons (DCX, 0.54±0.46%), FIG. 4E, and the rest of DsRed-infected cells were also microglia (39±7.7%) and NG2 cells (6.9±2.2%), but rarely oligodendrocytes (0.82±0.53%), FIG. 6. FIGS. 6A-6F show different glial cell types infected by retrovirus in the mouse cortex. In vivo immunostaining for astrocytes (GFAP), microglia (Iba1), NG2 cells (NG2), and oligodendrocytes (CNPase) after injecting DsRed into mouse cortex is shown in FIGS. 6A-C. In vivo immunostaining for astrocytes (GFAP), microglia (Iba1), NG2 cells (NG2), and oligodendrocytes (CNPase) after injecting NeuroD1-IRES-GFP retrovirus into mouse cortex is shown in FIGS. 6D-6F.

Figure 4F:
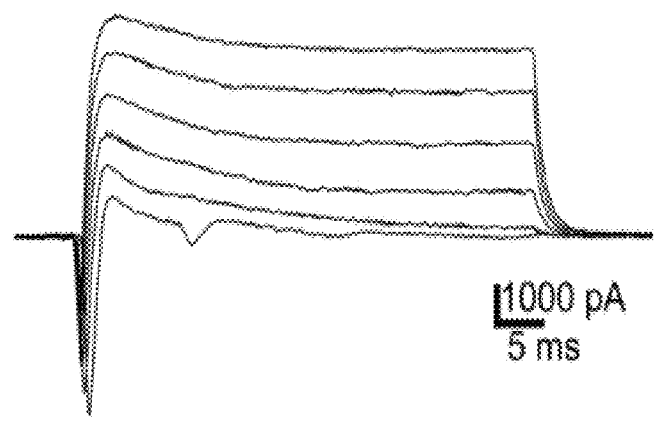
FIGS. 4F-4G show representative traces from cortical slice recordings showing $Na^+$ and $K^+$ currents (F) and repetitive action potentials (G) in NeuroD1-converted neurons (30 DPI)
Figure 4G:
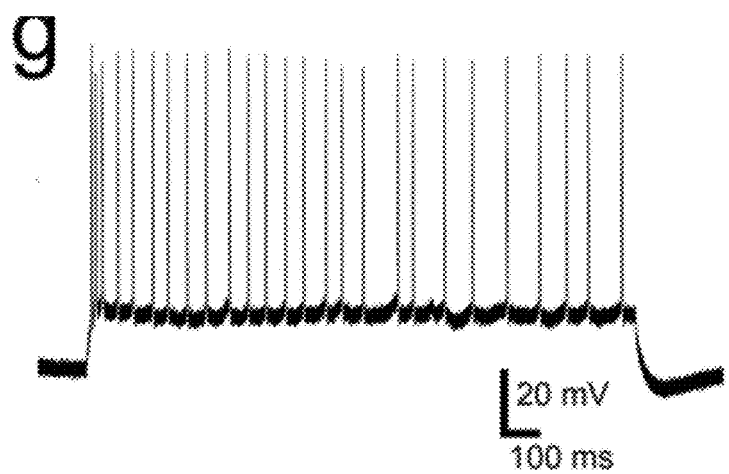
Figure 4H:
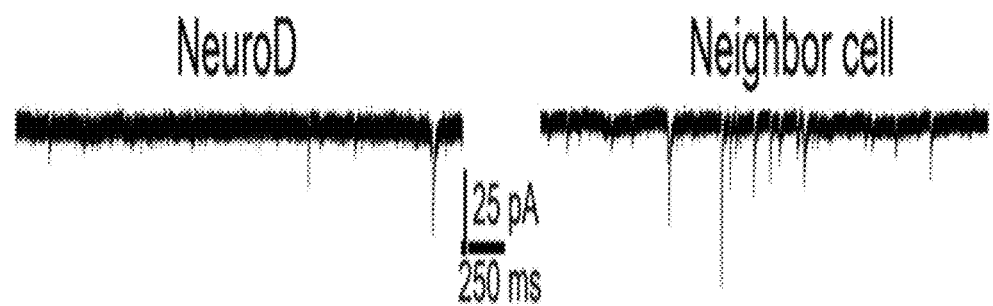
FIG. 4H shows representative traces of spontaneous synaptic events in an NeuroD1-transduced neuron and a neighboring control neuron in cortical slice recordings.

It was also confirmed that after stab injury, the NeuroD1-converted neurons in mouse brain in vivo were functional as revealed in cortical slice recordings, displaying large peak amplitude of $I_{Na}$ (3840±302 pA, n=5) and $I_K$ (4672±602 pA, n=5), FIG. 4F, and capable of firing repetitive action potentials, FIG. 4G. Moreover, spontaneous synaptic events were recorded in NeuroD1-transduced neurons in slice recordings (frequency, 0.31±0.01 Hz; amplitude, 18.8±0.4 pA; n=4; FIG. 4H), suggesting that they have been functionally incorporated into existing neural circuits. FIGS. 4F-4G show representative traces from cortical slice recordings showing $Na^+$ and $K^+$ currents (F) and repetitive action potentials (G) in NeuroD1-converted neurons (30 DPI). FIG. 4H shows representative traces of spontaneous synaptic events in a NeuroD1-transduced neuron and a neighboring control neuron in cortical slice recordings.

Example 12—Expression of Exogenous NeuroD1 in Astrocytes in an In Vivo Model of Alzheimer Disease An in vivo mouse model for Alzheimer disease is used in this example to examine the therapeutic potential of converting reactive astrocytes induced by Alzheimer disease into functional neurons to replenish the degenerated neurons. Reactive astrocytes have been widely reported in the cortex of Alzheimer's disease (AD) patients or animal models. A transgenic mouse model for AD (5xFAD), described in Oakley, H. et al., *J Neurosci* 26:10129-10140, 2006, was employed in this example to test whether reactive astrocytes in the AD brain can be converted into functional neurons. FIGS. 7A-7E show that NeuroD1 converts reactive astrocytes into neurons in AD mouse brain in vivo.

Figure 7A:
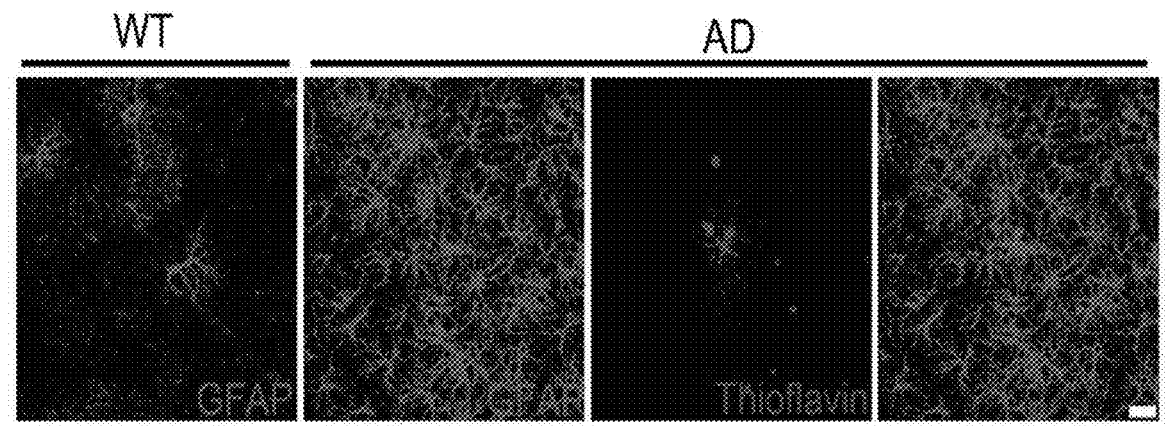
FIG. 7A shows reactive astrocytes labeled by GFAP in AD mouse cortex (5xFAD) were significantly increased compared to that in the WT cortex (6 month old), beta amyloid plaques were labeled by thioflavin-S.

It was first confirmed that there were indeed many reactive astrocytes in the cortex of 5xFAD mice compared to the WT, FIG. 7A. FIG. 7A shows reactive astrocytes labeled by GFAP in AD mouse cortex (5xFAD) were significantly increased compared to that in the WT cortex (6 month old). Beta amyloid plaques were labeled by thioflavin-S, scale bar, 20 μm.

Figure 7B:
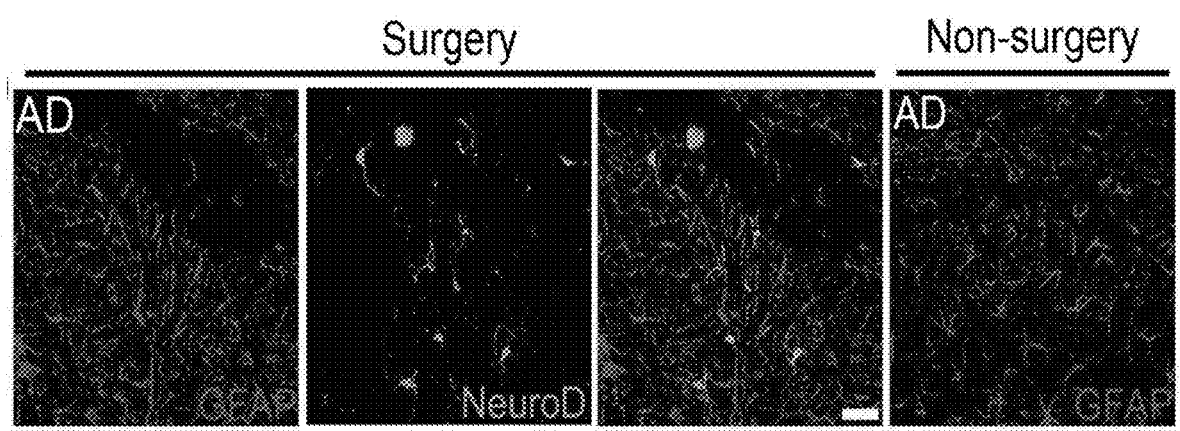
FIG. 7B shows NeuroD1-infected neuron-like cells (14 DPI) interspersed with reactive astrocytes (GFAP) in AD mouse cortex (5 month old)

Next, NeuroD1 retrovirus referred to in example 2 was injected into the cortex of 5xFAD mice (5 month old). Two weeks after the injection, neuron-like cells intermingled with the GFAP-labeled reactive astrocytes in the cortex of 5xFAD mice, FIG. 7B, were observed. FIG. 7B shows NeuroD1-infected neuron-like cells (14 DPI) interspersed with reactive astrocytes (GFAP) in AD mouse cortex (5 month old), scale bar, 40 μm.

Figure 7C:
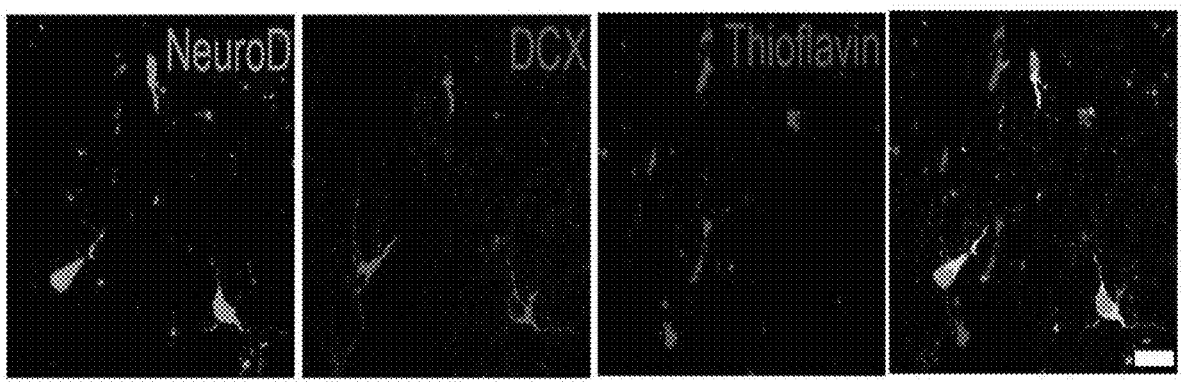
FIG. 7C shows high magnification images showing NeuroD1-converted cells labeled by DCX and close to the amyloid plaques.

Indeed, immunostaining with DCX confirmed that the NeuroD1-transduced cells in the AD brain were newborn neurons, and they were in the vicinity of Aβ plaques labeled by thioflavin-S, FIG. 7C. FIG. 7C shows high magnification images showing NeuroD1-converted cells labeled by DCX and close to the amyloid plaques (14 DPI), scale bar, 20 μm.

Figure 7D:
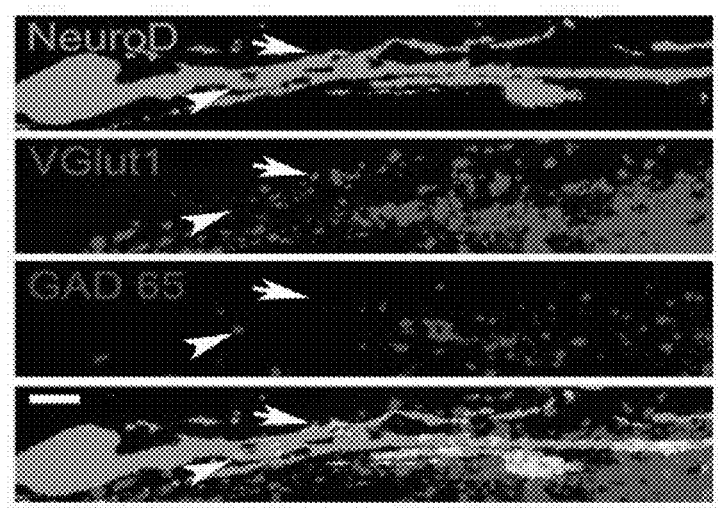
FIG. 7D shows NeuroD1-converted neurons in the AD brain were innervated by glutamatergic and GABAergic terminals.

Further immunostaining with VGluT1 and GAD65 found that the NeuroD1-transduced neurons in the AD brain were synaptically innervated by glutamatergic and GABAergic terminals, FIG. 7D. FIG. 7D shows NeuroD1-converted neurons in the AD brain were innervated by glutamatergic and GABAergic terminals (arrow points to a VGlut1 punctum, and arrowhead points to a GAD65 punctum), scale bar, 5 μm.

Figure 7E:
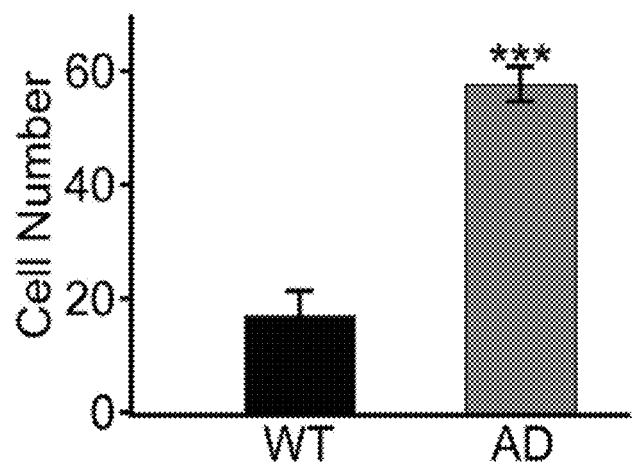
FIG. 7E shows quantification of the number of NeuroD1-converted neurons in WT and AD mouse brains.
Figure 7F:
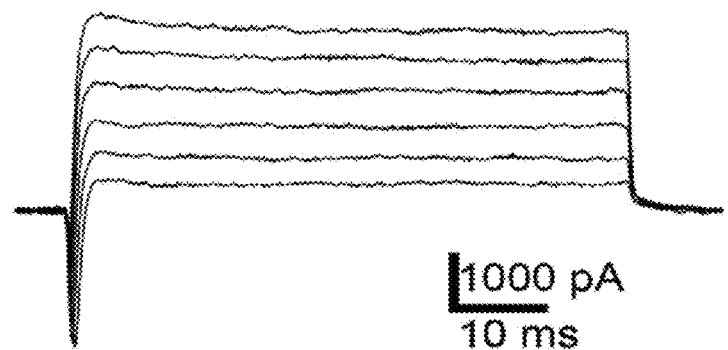
FIG. 7F shows the converted neurons in AD mouse brain in vivo are functional, illustrated by large $Na^+$ and $K^+$ currents.
Figure 7G:
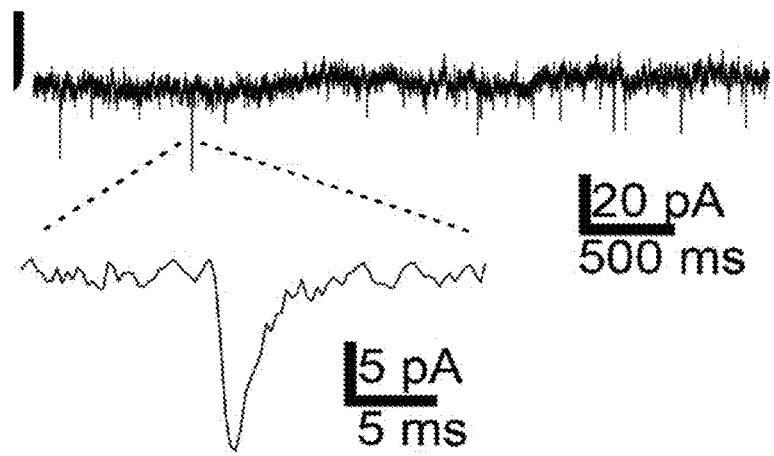
FIG. 7G shows the converted neurons in AD mouse brain in vivo are functional, illustrated spontaneous synaptic events.
Figure 8A:
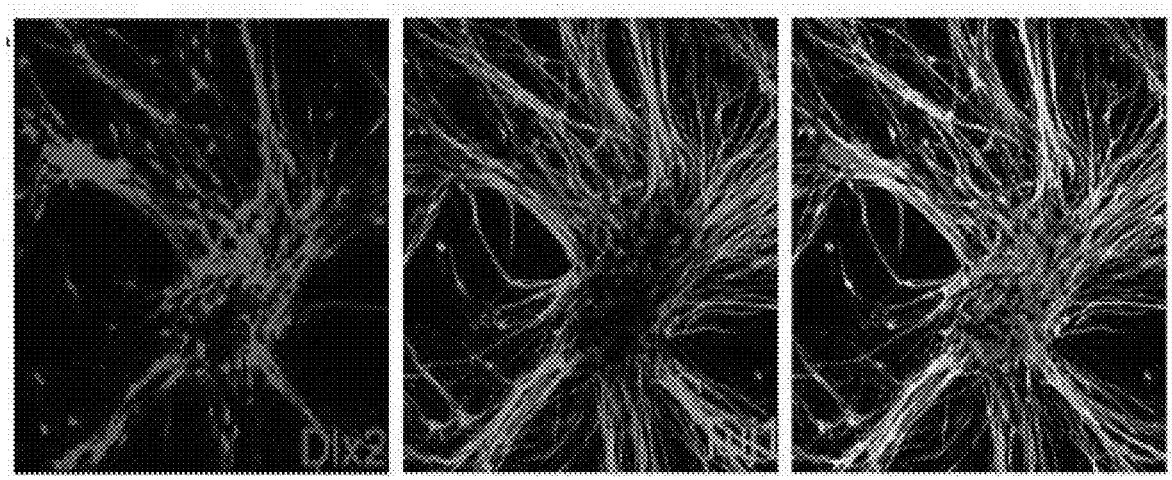
FIGS. 8A-8F show that expression of exogenous Dlx2 in cultured human astrocytes changed astrocytes into GAD-positive GABAergic neuron.
Figure 8B:
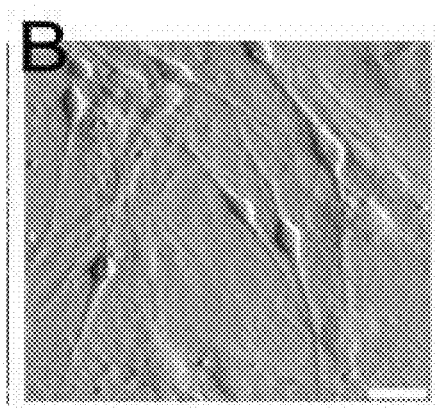
Figure 8C:
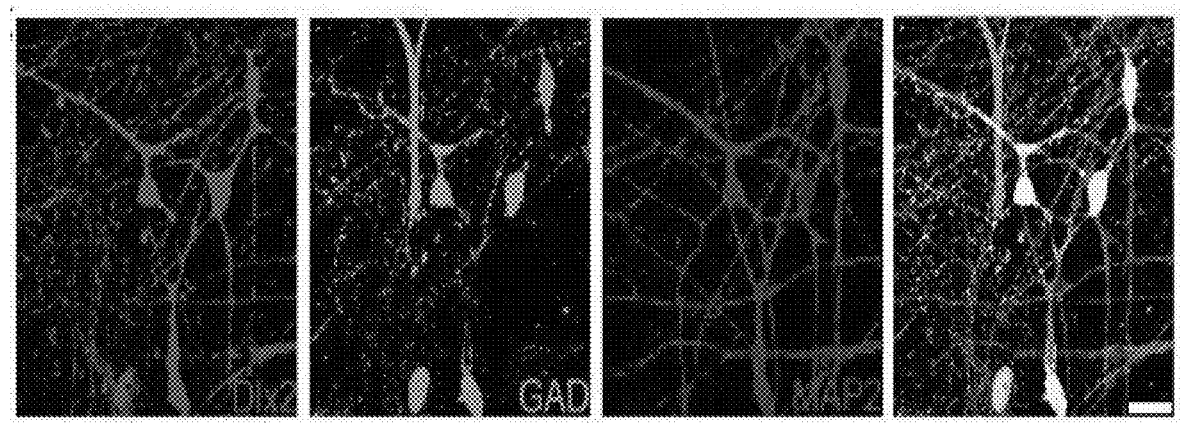
Figure 8D:
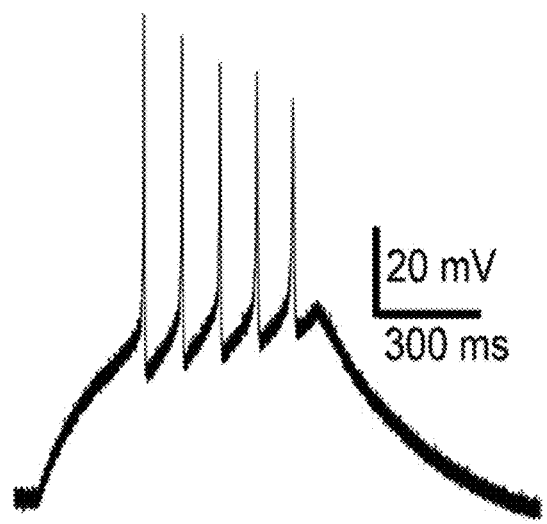
Figure 8E:
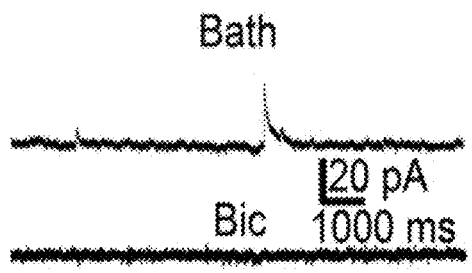
Figure 8F:
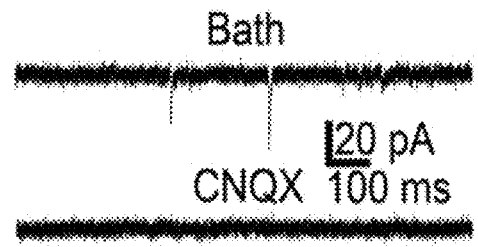

Quantitative comparison of the WT and AD brains (5 months old) after NeuroD1 infection shows that the number of NeuroD1-transduced neurons in the AD brain was significantly higher than that in the WT brain, FIG. 7E, likely due to more reactive astrocytes in the AD brain, FIG. 7A. FIG. 7E shows quantification of the number of NeuroD1-converted neurons in WT and AD mouse brains (n=4 animals, 5 months old). Importantly, the converted neurons in AD mouse brain in vivo are functional, as illustrated by large $Na^+$ and $K^+$ currents (FIG. 7F) and spontaneous synaptic events (FIG. 7G). Thus the reactive astrocyte-converted neurons replace the lost neurons and restore brain functions in the AD brain.

Example 13—Animal Model of Focal Ischemic Stroke 1

In this example, a mouse model for endothelin-1 induced focal ischemic stroke is used to determine the effects of expression of exogenous NeuroD1 in glial cells in the stroke injured brain.

Animals: 3-5 month old C57BL/6 male mice (20-30 gram) are housed in standard cage of animal facility of Penn State University on a 12:12 light/dark cycle. Mice are maintained on a restricted feeding schedule (3 g/day) to prevent satiation and motivate reaching performance. One group of mice receives intracortical infusions of endothelin-1 (ET-1); one group of mice receives intracortical infusions of 0.9% sterile saline; one group of mice receives sham procedures.

Surgery procedure: Mice are anesthetized by using 0.25% Avertin (dissolved in sterile saline, 20 ml/kg, i.p.). Tail/foot pinch and corneal response is tested to verify full anesthetization. Temperature is maintained at 37° C. through a thermal pad during surgery. The scalp is shaved and cleaned with iodine, then injected with bupivacaine (1 ml/20 g, s.c.). Each mouse is then placed in a stereotaxic apparatus; a midline incision is made along the length of shaved area. A small burr hole is drilled through the skull over the center of the forelimb region of the sensorimotor cortex at coordinates of 2.25 mm lateral to midline and +0.6 mm anterior to Bregma. The dura mater is punctured and a 1 ml syringe with a 26 gauge needle is lowered into the cortex to a depth of 700 µm. 4 µl of ET-1 (320 pmol, 0.2 µg/µl in sterile saline) is injected into the cortex for 10 min, and the syringe is left in place for 5 min post-injection to prevent backflow before slowly removed. The burr hole is then filled with gelfoam and covered with UV curing dental cement, and the wound is sutured and covered in antibiotic ointment. After surgery the animal is placed on the thermal pad till fully awaken before returning to its home cage. Of the two sham groups, one group receives all surgical procedures up to the skull opening and the other receives a skull opening and infusion of vehicle (0.9% sterile saline) into the forelimb area of the sensorimotor cortex. Mice are checked in the following days (4-5 days) after surgery to ensure the normal recovery of mice.

A behavioral test, the bilateral tactile stimulation test, can be used to assess the induced stroke. For this test, each mouse is placed into a shallow transparent plastic container (8.5 cm tall, 18 cm in diameter) with an open top and allowed to habituate for 1 min. The mouse is picked up and lightly restrained by the scruff while a 1.27 cm long piece of 3 mm wide tape is placed onto the ventral side of each paw. The mouse is then placed back into the container and allowed to remove each piece of tape using its teeth. The latency to contact and remove each piece of tape is recorded for five trials, allowing 30 s of rest between each trial.

NeuroD1 retrovirus including SEQ ID NO: 2 or SEQ ID NO: 4 is generated as described in Example 2 and injected into the cortex of mice as described in Example 5. After about two weeks following the injection of NeuroD1, the brains will be examined to confirm an increase in neurons in the vicinity of the NeuroD1 retrovirus injection. The bilateral tactile stimulation test can be used to assess improvement of stroke-related behavioral effects.

Example 14—Animal Model of Focal Ischemic Stroke II

In this example, a mouse model for photothrombosis-induced focal ischemic stroke is used to determine the effects of expression of exogenous NeuroD1 in glial cells in the stroke injured brain.

Animals: 3-5 month old C57BL/6 male mice (20-30 gram) are housed in standard cage of animal facility of Penn State University on a 12:12 light/dark cycle. Mice are maintained on a restricted feeding schedule (3 g/day) to prevent satiation and motivate reaching performance. Surgery procedure: Mice are anesthetized by using 0.25% Avertin (dissolved in sterile saline, 20 ml/kg body weight, i.p.). Tail/foot pinch and corneal response is tested to verify full anesthetization. Temperature is maintained at 37° C. through a thermal pad during surgery. The skin above the skull is incised, and a fiber-optic bundle mounted on a cold light source (diameter 1.5 mm, wavelength 560 nm, aperture B2, 1750K, KL 1500 LCD) is placed over the right hemisphere with a focus at 2.25 mm lateral to midline and +0.6 mm anterior to Bregma. The photosensitive dye rose Bengal (dissolved in artificial cerebral spinal fluid) is injected into the lateral tail vein (30 mg/kg body weight). Focal illumination of the skull starts immediately after the injection, which lasts for 20 min. After the induction of thrombosis, the incision is sutured and the animal is placed on the thermal pad till fully awaken before returning to its home cage. The placement of the light beam, the light intensity, and the light aperture are the same for all animals. Of the sham group, mice receive all surgical procedures except for light irradiation. Mice are checked in the following days (4-5 days) after surgery to ensure the normal recovery of mice.

A behavioral test, the bilateral tactile stimulation test, can be used to assess the induced stroke. For this test, each mouse is placed into a shallow transparent plastic container (8.5 cm tall, 18 cm in diameter) with an open top and allowed to habituate for 1 min. The mouse is picked up and lightly restrained by the scruff while a 1.27 cm long piece of 3 mm wide tape is placed onto the ventral side of each paw. The mouse is then placed back into the container and allowed to remove each piece of tape using its teeth. The latency to contact and remove each piece of tape is recorded for five trials, allowing 30 s of rest between each trial.

NeuroD1 retrovirus including SEQ ID NO: 2 or SEQ ID NO: 4 is generated as described in Example 2 and injected into the cortex of mice as described in Example 5. After about two weeks following the injection of NeuroD1, the brains will be examined to confirm an increase in neurons in the vicinity of the NeuroD1 retrovirus injection. The bilateral tactile stimulation test can be used to assess improvement of stroke-related behavioral effects.

Example 15—Animal Model of Spinal Cord Injury

In this example, a mouse model for spinal cord injury is used to determine the effects of expression of exogenous NeuroD1 in glial cells in the injured spinal cord.

Animals to be used in this example are female C57B/6 mice (22-29 g) Prior to surgery a heating pad is pre-heated to maintain a temperature range of 36.6-37.1° C. throughout the whole surgery process. Mice are anesthetized by injecting 15 ml/kg 0.25% Avertin into the peritoneum. After mouse is immobilized shave the skin of back. Cover eyes with ointment. Place the mouse on the heating pad with back up, disinfecting the back twice with 70% alcohol. Before proceeding the mouse is checked to insure that there is no reflex to a toe pinch. Then, a 1.3 cm dorsal median incision is to be made over the thoracic vertebral column incision on the back. The caudal part of the nuchal ligament and the underlying trapezius muscle from its origin of the spinal processes is cut to expose the spinous processes of T8-T10. A fine pair of rongeurs is used to make a laminectomy of vertebra T9-T10, being careful not to damage the dura. Once the spinal cord is exposed, either of two methods will be used for injury: 1) using a pair of forceps, the spinal process of T9 is held and lifted to open the intervertebral space. A pair of modified forceps is used to laterally compress the spinal cord to the thickness of 0.3 mm and is held with the forceps for 15 sec or 2) a pair of forceps is used to hold and slightly lift the spinal process of T9 to open the intervertebral space. The cord is transected with a microscalpel (5 mm blade depth, 15°; Roboz Surgical Instruments) in one movement from the right to the left. The cut is redone a second time from the left to the right taking great care to slide with the tip of the scalpel over the osseous surface of the spinal canal to ensure complete transection. A sham injury control group will receive identical treatment, including exposure, laminectomy and placement of the forceps around the spinal cord, but no crush or transaction injury would be inflicted. The breath and heartbeat of each animal is monitored throughout the whole surgery procedure. Then, the autochtone muscles and the trapezius muscles of both sides are repositioned and gently opposed muscles by closed three single sutures using 10-0 Ethilon (7718G, Ethicon). The skin is closed with the same suture.

Post surgery care: each mouse is kept on a heating pad until it wakes up after which it is transferred to its cage with bedding, enough water and soft food.

Immediately following the surgery and for an additional day, 1 ml Ringer's solution for hydration and buprenorphine (0.01 mg/kg) will be subcutaneously injected twice daily for 3 days to alleviate pain. Each mouse is checked every day post-surgery and the bladder manually evacuated twice daily until the mouse can spontaneously micturate. Each mouse will be intraperitoneally injected with 0.01 ml antibiotics Baytril to prevent bladder infection.

NeuroD1 retrovirus including SEQ ID NO: 2 or SEQ ID NO: 4 is generated as described in Example 2 and will be injected into the spinal cord of mice at the site of the spinal cord injury. After about two weeks following the injection of NeuroD1, the spinal cords will be examined to confirm an increase in neurons in the vicinity of the NeuroD1 retrovirus injection.

Example 16—Effect of Expression of Exogenous Dlx2 Converted Human Astrocytes into GABAergic and Glutamatergic Neurons in Cell Culture FIGS. 8A-8F show that expression of exogenous Dlx2 in cultured human astrocytes changed astrocytes into GAD-positive GABAergic neurons, which showed repetitive action potentials and GABAergic events. Occasionally, some glutamatergic events were also detected, suggesting that Dlx2 can convert human astrocytes into both GABAergic and glutamatergic neurons.

Example 17—Converting Reactive Astrocytes into Neurons in Non-Human Primates Conversion of reactive astrocytes into neurons will be performed using non-human primates, such as marmoset or macaque monkeys, to introduce human NeuroD1 into reactive astrocytes after stroke (similar to that described in Example 13 and 14) or spinal cord injury (similar to that described in Example 15) to convert them into functional neurons. NeuroD1 can be introduced into animals through retrovirus or adeno-associated virus that contain astroglial specific promoter GFAP to allow expression of NeuroD1 only in astrocytes. Nanoparticles that can bind with plasmids or viral particles can also be used to introduce NeuroD1 into glial cells for neuronal conversion.

Sequences

```
SEQ ID NO: 1 - Human NeuroD1 nucleic acid
sequence encoding human NeuroD1 protein -
1071 nucleotides, including stop codon
atgaccaaatcgtacagcgagagtgggctgatgggcgagcctcagcccca aggtcctccaagctggacagacgagtgtctcagttctcaggacgaggagc acgaggcagacaagaaggaggacgacctcgaagccatgaacgcagaggag gactcactgaggaacggggggagaggaggaggacgaagatgaggacctgga agaggaggaagaagaggaagaggaggatgacgatcaaaagcccaagagac gcggccccaaaagaagaagatgactaaggctcgcctggagcgttttaaa ttgagacgcatgaaggctaacgcccgggagcggaaccgcatgcacggact gaacgcggcgctagacaacctgcgcaaggtggtgccttgctattctaaga cgcagaagctgtccaaaatcgagactctgcgcttggccaagaactacatc tgggctctgtcggagatcctgcgctcaggcaaaagcccagacctggtctc cttcgttcagacgctttgcaagggcttatcccaacccaccaccaacctgg ttgcgggctgcctgcaactcaatcctcggacttttctgcctgagcagaac caggacatgcccccccacctgccgacggccagcgcttccttccctgtaca cccctactcctaccagtcgcctgggctgcccagtccgccttacggtacca tggacagctcccatgtcttccacgttaagcctccgccgcacgcctacagc gcagcgctggagcccttctttgaaagccctctgactgattgcaccagccc ttcctttgatggacccctcagcccgccgctcagcatcaatggcaacttct ctttcaaacacgaaccgtccgccgagtttgagaaaaattatgccttacc atgcactatcctgcagcgacactggcaggggcccaaagccacggatcaat cttctcaggcaccgctgcccctcgctgcgagatccccatagacaatatta tgtccttcgatagccattcacatcatgagcgagtcatgagtgcccagctc aatgccatatttcatgattag SEQ ID NO: 2 - Human NeuroD1 amino acid
sequence - 356 amino acids - encoded
by SEQ ID NO: 1
MTKSYSESGLMGEPQPQGPPSWTDECLSSQDEEHEADKKEDDLEAMNAEE

DSLRNGGEEEDEDEDLEEEEEEEEDDDQKPKRRGPKKKKMTKARLERFK

LRRMKANARERNRMHGLNAALDNLRKVVPCYSKTQKLSKIETLRLAKNYI

WALSEILRSGKSPDLVSFVQTLCKGLSQPTTNLVAGCLQLNPRTFLPEQN

QDMPPHLPTASASFPVHPYSYQSPGLPSPPYGTMDSSHVFHVKPPPHAYS

AALEPFFESPLTDCTSPSFDGPLSPPLSINGNFSFKHEPSAEFEKNYAFT

MHYPAATLAGAQSHGSIFSGTAAPRCEIPIDNIMSFDSHSHHERVMSAQL

NAIFHD

SEQ ID NO: 3 - Mouse NeuroD1 nucleic acid
sequence encoding mouse NeuroD1 protein -
1074 nucleotides, including stop codon
atgaccaaatcatacagcgagagcgggctgatgggcgagcctcagcccca aggtcccccaagctggacagatgagtgtctcagttctcaggacgaggaac acgaggcagacaagaaagaggacgagcttgaagccatgaatgcagaggag gactctctgagaaacggggggagaggaggaggaggaagatgaggatctaga ggaagaggaggaagaagaagaggaggaggaggatcaaaagcccaagagac
```

```
gggtcccaaaaagaaaaagatgaccaaggcgcgcctagaacgttttaaa ttaaggcgcatgaaggccaacgcccgcgagcggaaccgcatgcacgggct gaacgcggcgctggacaacctgcgcaaggtggtaccttgctactccaaga cccagaaactgtctaaaatagagacactgcgcttggccaagaactacatc tgggctctgtcagagatcctgcgctcaggcaaaagccctgatctggtctc cttcgtacagacgctctgcaaaggtttgtcccagcccactaccaatttgg tcgccggctgcctgcagctcaaccctcggactttcttgcctgagcagaac ccggacatgcccccgcatctgccaaccgccagcgcttccttcccggtgca tccctactcctaccagtccctggactgcccagcccgccctacggcacca tggacagctcccacgtcttccacgtcaagccgccgccacacgcctacagc gcagctctggagcccttctttgaaagcccctaactgactgcaccagccc ttcctttgacggaccctcagcccgccgctcagcatcaatggcaacttct ctttcaaacacgaaccatccgccgagtttgaaaaaattatgcctttacc atgcactaccctgcagcgacgctggcagggccccaaagccacggatcaat cttctcttccggtgccgctgcccctcgctgcgagatccccatagacaaca
```

```
ttatgtctttcgatagccattcgcatcatgagcgagtcatgagtgcccag cttaatgccatctttcacgattag
```

SEQ ID NO: 4 - Mouse NeuroD1 amino acid
sequence - 357 amino acids - encoded
by SEQ ID NO: 3
MTKSYSESGLMGEPQPQGPPSWTDECLSSQDEEHEADKKEDELEAMNAEE

DSLRNGGEEEEEDEDLEEEEEEEEEEDQKPKRRGPKKKKMTKARLERFK

LRRMKANARERNRMHGLNAALDNLRKVVPCYSKTQKLSKIETLRLAKNYI

WALSEILRSGKSPDLVSFVQTLCKGLSQPTTNLVAGCLQLNPRTFLPEQN

PDMPPHLPTASASFPVHPYSYQSPGLPSPPYGTMDSSHVFHVKPPPHAYS

AALEPFFESPLTDCTSPSFDGPLSPPLSINGNFSFKHEPSAEFEKNYAFT

MHYPAATLAGPQSHGSIFSSGAAAPRCEIPIDNIMSFDSHSHHERVMSAQ

LNAIFHD

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating stroke, comprising: administering a therapeutically effective dose of a viral vector comprising a nucleic acid sequence encoding a NeuroD1 protein by intracerebral injection to the brain of an adult mammalian subject; whereby said NeuroD1 protein is expressed in reactive astrocytes, and wherein the number of reactive astrocytes is reduced, and the number of neurons is increased within said subject compared to an untreated subject having a stroke.

2. The method of claim 1, wherein said nucleic acid sequence comprises a nucleic acid sequence selected from the group consisting of: a nucleic acid sequence encoding SEQ ID NO:2; a nucleic acid sequence encoding SEQ ID NO:4; SEQ ID NO:1; SEQ ID NO:3; and a nucleic acid sequence encoding a protein which has 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or greater, identity to SEQ ID NO: 2 or SEQ ID NO: 4.

3. The method of claim 1, wherein said NeuroD1 protein comprises the amino acid sequence set forth in SEQ ID NO:2.

4. The method of claim 1, wherein said subject is a human.

5. The method of claim 1, wherein said viral vector is an adeno-associated viral vector.

* * * * *